(12) United States Patent
Lowe et al.

(10) Patent No.: US 8,079,364 B2
(45) Date of Patent: Dec. 20, 2011

(54) DEPLOYMENT ACTUATION SYSTEM FOR INTRAFALLOPIAN CONTRACEPTION

(75) Inventors: Christian Lowe, San Francisco, CA (US); Don Gurskis, Redwood City, CA (US); Ashish Khera, San Francisco, CA (US); Monica Barnhart, Foster City, CA (US); Steven Bacich, Half Moon Bay, CA (US); Betsy Swann, Newark, CA (US); Roberto Silva-Torres, Foster City, CA (US)

(73) Assignee: Conceptus, Inc., Mountain View, CA (US)

( * ) Notice: Subject to any disclaimer, the term of this patent is extended or adjusted under 35 U.S.C. 154(b) by 0 days.

(21) Appl. No.: 13/073,910

(22) Filed: Mar. 28, 2011

(65) Prior Publication Data

US 2011/0226257 A1  Sep. 22, 2011

Related U.S. Application Data

(63) Continuation of application No. 12/506,953, filed on Jul. 21, 2009, now Pat. No. 7,934,504, which is a continuation of application No. 11/154,144, filed on Jun. 15, 2005, now Pat. No. 7,591,268, which is a continuation of application No. 10/785,553, filed on Feb. 23, 2004, now Pat. No. 7,506,650, which is a continuation of application No. 09/644,287, filed on Aug. 22, 2000, now Pat. No. 6,709,667.

(60) Provisional application No. 60/150,238, filed on Aug. 23, 1999.

(51) Int. Cl.
*A61F 6/06* (2006.01)

(52) U.S. Cl. ...................................... 128/830; 128/831
(58) Field of Classification Search .......... 128/830–841
See application file for complete search history.

(56) References Cited

U.S. PATENT DOCUMENTS

| 2,102,270 A | 12/1937 | Hyams |
| 3,042,030 A | 7/1962 | Read |
| 3,561,438 A | 2/1971 | Canel |

(Continued)

FOREIGN PATENT DOCUMENTS

CN  1047447  5/1990

(Continued)

OTHER PUBLICATIONS

Brueschke, E.E., et al. "Transcervical tubal occlusion with a steerable hysteroscope: Implantation of devices into extirpated human uteri," *Am. J. Obstet. Gynecol.* vol. 127, No. 2, pp. 118-124, 1977.

(Continued)

*Primary Examiner* — Michael A. Brown
(74) *Attorney, Agent, or Firm* — Blakely, Sokoloff, Taylor & Zafman LLP

(57) ABSTRACT

Contraceptive methods, systems, and devices generally improve the ease, speed, and reliability with which a contraceptive device can be deployed transcervically into an ostium of a fallopian tube. The contraceptive device may remain in a small profile configuration while a sheath is withdrawn proximally, and is thereafter expanded to a large profile configuration engaging the surrounding tissues, by manipulating one or more actuators of a proximal handle with a single hand. This leaves the other hand free to manipulate a hysteroscope, minimizing the number of health care professional required to deploy the contraceptive device.

16 Claims, 27 Drawing Sheets

U.S. PATENT DOCUMENTS

| | | | |
|---|---|---|---|
| 3,563,235 A | 2/1971 | Zipper |
| 3,566,874 A | 3/1971 | Shepherd et al. |
| 3,687,129 A | 8/1972 | Nuwayser |
| 3,763,856 A | 10/1973 | Blomberg |
| 3,774,600 A | 11/1973 | Cognat |
| 3,805,767 A | 4/1974 | Erb |
| 3,840,016 A | 10/1974 | Lindemann |
| 3,858,571 A | 1/1975 | Rudolph |
| 3,858,586 A | 1/1975 | Lessen |
| 3,895,634 A | 7/1975 | Berger et al. |
| 3,918,431 A | 11/1975 | Sinnreich |
| 3,938,527 A | 2/1976 | Rioux et al. |
| 3,973,560 A | 8/1976 | Emmett |
| 4,003,380 A | 1/1977 | Wien |
| RE29,345 E | 8/1977 | Erb |
| 4,040,417 A | 8/1977 | Zipper |
| 4,057,063 A | 11/1977 | Gieles et al. |
| 4,111,196 A | 9/1978 | Emmett |
| 4,136,695 A | 1/1979 | Dafoe |
| 4,140,126 A | 2/1979 | Choudhury |
| 4,143,656 A | 3/1979 | Holmes |
| 4,185,618 A | 1/1980 | Corey |
| 4,207,891 A | 6/1980 | Boldue |
| 4,246,896 A | 1/1981 | Horne, Jr. et al. |
| 4,353,363 A | 10/1982 | Sopena Quesada |
| 4,365,621 A | 12/1982 | Brundin |
| 4,416,660 A | 11/1983 | Dafoe |
| 4,503,569 A | 3/1985 | Dotter |
| 4,509,504 A | 4/1985 | Brundin |
| 4,523,590 A | 6/1985 | Roth et al. |
| 4,537,186 A | 8/1985 | Verschoof et al. |
| 4,574,806 A | 3/1986 | McCarthy |
| 4,579,110 A | 4/1986 | Hamou |
| 4,595,000 A | 6/1986 | Hamou |
| 4,606,336 A | 8/1986 | Zeluff |
| 4,612,924 A | 9/1986 | Cimber |
| 4,628,924 A | 12/1986 | Cimber |
| 4,638,803 A | 1/1987 | Rand |
| 4,655,771 A | 4/1987 | Wallsten |
| 4,700,701 A | 10/1987 | Montaldi |
| 4,717,387 A | 1/1988 | Inoue et al. |
| 4,727,866 A | 3/1988 | Livesay et al. |
| 4,733,665 A | 3/1988 | Palmaz |
| 4,788,966 A | 12/1988 | Yoon |
| 4,921,483 A | 5/1990 | Wijay et al. |
| 4,932,421 A | 6/1990 | Kaali et al. |
| 4,943,290 A | 7/1990 | Rexroth et al. |
| 4,969,458 A | 11/1990 | Wiktor |
| 4,994,069 A | 2/1991 | Ritchart et al. |
| 5,065,751 A | 11/1991 | Wolf |
| 5,071,407 A | 12/1991 | Termin et al. |
| 5,095,917 A | 3/1992 | Vancaillie |
| 5,108,420 A | 4/1992 | Marks |
| 5,122,136 A | 6/1992 | Guglielmi et al. |
| 5,122,137 A | 6/1992 | Lennox |
| 5,133,709 A | 7/1992 | Prince |
| 5,147,353 A | 9/1992 | Everett |
| 5,147,370 A | 9/1992 | McNamara et al. |
| 5,163,958 A | 11/1992 | Pinchuk |
| 5,176,692 A | 1/1993 | Wilk et al. |
| 5,192,301 A | 3/1993 | Kamiya et al. |
| 5,207,684 A | 5/1993 | Nobles |
| 5,226,911 A | 7/1993 | Chee et al. |
| 5,234,437 A | 8/1993 | Sepetka |
| 5,244,096 A | 9/1993 | Stoner |
| 5,250,071 A | 10/1993 | Palermo |
| 5,261,916 A | 11/1993 | Engelson |
| 5,303,719 A | 4/1994 | Wilk et al. |
| 5,304,194 A | 4/1994 | Chee et al. |
| 5,304,195 A | 4/1994 | Twyford, Jr. et al. |
| 5,304,228 A | 4/1994 | Prince |
| 5,312,356 A | 5/1994 | Engelson et al. |
| 5,312,415 A | 5/1994 | Palermo |
| 5,342,348 A | 8/1994 | Kaplan |
| 5,346,498 A | 9/1994 | Greelis et al. |
| 5,350,397 A | 9/1994 | Palermo et al. |
| 5,354,295 A | 10/1994 | Guglielmi et al. |
| 5,354,309 A | 10/1994 | Schnepp-Pesch et al. |
| 5,356,388 A | 10/1994 | Sepetka et al. |
| 5,364,393 A | 11/1994 | Auth et al. |
| 5,382,259 A | 1/1995 | Phelps et al. |
| 5,382,260 A | 1/1995 | Dormandy et al. |
| 5,389,100 A | 2/1995 | Bacich et al. |
| 5,411,549 A | 5/1995 | Peters |
| 5,423,829 A | 6/1995 | Pham et al. |
| 5,423,849 A | 6/1995 | Engelson et al. |
| 5,441,485 A | 8/1995 | Peters |
| 5,443,500 A | 8/1995 | Sigwart |
| 5,458,636 A | 10/1995 | Brancato |
| 5,474,089 A | 12/1995 | Waynant |
| 5,499,995 A | 3/1996 | Teirstein |
| 5,507,768 A | 4/1996 | Lau et al. |
| 5,514,176 A | 5/1996 | Bosley, Jr. |
| 5,522,822 A | 6/1996 | Phelps et al. |
| 5,522,836 A | 6/1996 | Palermo |
| 5,534,007 A | 7/1996 | St. Germain et al. |
| 5,545,210 A | 8/1996 | Hess et al. |
| 5,549,624 A | 8/1996 | Mirigian et al. |
| 5,556,396 A | 9/1996 | Cohen et al. |
| 5,562,641 A | 10/1996 | Flomenblit et al. |
| 5,569,245 A | 10/1996 | Guglielmi et al. |
| 5,578,074 A | 11/1996 | Mirigian |
| 5,582,619 A | 12/1996 | Ken |
| 5,601,593 A | 2/1997 | Freitag |
| 5,601,600 A | 2/1997 | Ton |
| 5,624,449 A | 4/1997 | Pham et al. |
| 5,624,461 A | 4/1997 | Mariant |
| 5,630,797 A | 5/1997 | Diedrich et al. |
| 5,656,036 A | 8/1997 | Palmaz |
| 5,690,666 A | 11/1997 | Berenstein et al. |
| 5,690,842 A | 11/1997 | Panchinson |
| 5,718,711 A | 2/1998 | Berenstein et al. |
| 5,743,905 A | 4/1998 | Eder et al. |
| 5,746,692 A | 5/1998 | Bacich et al. |
| 5,746,769 A | 5/1998 | Ton et al. |
| 5,755,773 A | 5/1998 | Evans et al. |
| 5,766,160 A | 6/1998 | Samson et al. |
| 5,772,669 A | 6/1998 | Vrba |
| 5,807,236 A | 9/1998 | Bacich et al. |
| 5,843,158 A | 12/1998 | Lenker et al. |
| 5,876,373 A | 3/1999 | Giba et al. |
| 5,895,749 A | 4/1999 | Alvarez |
| 5,897,551 A | 4/1999 | Everett et al. |
| 5,925,059 A | 7/1999 | Palermo et al. |
| 5,935,137 A | 8/1999 | Saadat et al. |
| 5,954,715 A | 9/1999 | Harrington et al. |
| 5,968,052 A | 10/1999 | Sullivan, III et al. |
| 5,976,162 A | 11/1999 | Doan et al. |
| 6,019,757 A | 2/2000 | Scheldrup |
| 6,027,863 A | 2/2000 | Donadio, III |
| 6,042,590 A | 3/2000 | Sporri et al. |
| 6,066,139 A | 5/2000 | Ryan et al. |
| 6,068,626 A | 5/2000 | Harrington et al. |
| 6,080,152 A | 6/2000 | Nardella et al. |
| 6,096,052 A | 8/2000 | Callister et al. |
| 6,143,007 A | 11/2000 | Mariant et al. |
| 6,145,505 A | 11/2000 | Nikolchev et al. |
| 6,156,742 A | 12/2000 | Mackenzie |
| 6,176,240 B1 | 1/2001 | Nikolchev et al. |
| 6,178,354 B1 | 1/2001 | Gibson |
| 6,187,027 B1 | 2/2001 | Mariant et al. |
| 6,245,053 B1 | 6/2001 | Benjamin |
| 6,270,495 B1 | 8/2001 | Palermo |
| 6,309,384 B1 | 10/2001 | Harrington et al. |
| 6,315,715 B1 | 11/2001 | Taylor et al. |
| 6,432,116 B1 | 8/2002 | Callister et al. |
| 6,482,171 B1 | 11/2002 | Corvi et al. |
| 6,526,979 B1 | 3/2003 | Nikolchev et al. |
| 6,565,557 B1 | 5/2003 | Sporri et al. |
| 6,585,663 B1 | 7/2003 | Coley et al. |
| 6,634,361 B1 | 10/2003 | Nikolchev et al. |
| 6,709,667 B1 * | 3/2004 | Lowe et al. ............ 424/422 |
| 6,726,682 B2 | 4/2004 | Harrington et al. |
| 6,763,833 B1 | 7/2004 | Khera et al. |
| 7,309,334 B2 | 12/2007 | von Hoffmann |
| 7,354,428 B1 | 4/2008 | Gosiengfiao et al. |
| 7,506,650 B2 * | 3/2009 | Lowe et al. ............ 128/830 |

| | | | |
|---|---|---|---|
| 7,591,268 B2 * | 9/2009 | Lowe et al. | 128/830 |
| 7,934,504 B2 * | 5/2011 | Lowe et al. | 128/830 |
| 2003/0135198 A1 | 7/2003 | Berhow et al. | |

FOREIGN PATENT DOCUMENTS

| | | |
|---|---|---|
| DE | 28 03 685 A1 | 8/1979 |
| EP | 0 010 812 | 5/1980 |
| EP | 0105669 B1 | 9/1983 |
| EP | 0183372 A1 | 10/1985 |
| EP | 0421966 A1 | 9/1990 |
| EP | 0 739 608 A1 | 10/1996 |
| EP | 0 541 258 | 5/1997 |
| EP | 0 891 757 A2 | 1/1999 |
| GB | 1460077 | 12/1976 |
| GB | 2 010 728 | 7/1979 |
| GB | 2 038 186 | 7/1980 |
| GB | 2 211 095 | 6/1989 |
| GB | 2 221 095 | 6/1989 |
| JP | A-49-135486 | 12/1974 |
| JP | A-5-208051 | 8/1993 |
| NL | 7810696 | 4/1990 |
| WO | WO 80/02369 | 11/1980 |
| WO | WO 83/00011 A1 | 1/1983 |
| WO | WO 93/06884 | 4/1993 |
| WO | WO 94/06503 | 3/1994 |
| WO | WO 94/07560 | 4/1994 |
| WO | WO 94/10936 | 5/1994 |
| WO | WO 94/11051 | 5/1994 |
| WO | WO 94/24944 A1 | 11/1994 |
| WO | WO 95/01123 | 1/1995 |
| WO | WO 96/40023 | 12/1996 |
| WO | WO 96/40024 | 12/1996 |
| WO | WO 97/08997 | 3/1997 |
| WO | WO 97/13451 | 4/1997 |
| WO | WO 97/27893 | 8/1997 |
| WO | WO 97/32623 | 9/1997 |
| WO | WO 97/46175 A1 | 12/1997 |
| WO | WO 97/49345 | 12/1997 |
| WO | WO 98/26737 | 6/1998 |
| WO | WO 98/31308 A1 | 7/1998 |
| WO | WO 98/55046 | 12/1998 |
| WO | WO 99/15116 | 4/1999 |
| WO | WO 00/13624 | 3/2000 |
| WO | WO 01/13832 A1 | 1/2001 |
| WO | WO 03/004086 | 1/2003 |

OTHER PUBLICATIONS

Brueschkle, et al., "A Steerable Hysteroscopic and Mechanical Tubal Occlusive Devices", Advances in Female Sterilization Techniques, Eds., Harper & Row, Publishers, 1976, pp. 182-198.
Brueschke, Erich E., "Reversible Occlusive Devices," J. Reproductive Medicine for the Obstetrician and Gynecologist, vol. 17, No. 2 (Aug. 1976).
Brundin J., "Ch. 31: Hydrogel Tubal Blocking Device: P-Block," Female Transcervical Sterilization (Gerald Zatuchni, M.D. et al., eds., Harper & Row 1983).
Brundin, J., "Hysteroscopy for Sterilization," Contraceptive Delivery Systems: An International Journal (1982).
Brundin, J., "Observations on the mode of action of an intratubal device, the P-block," Am. J. of Obst. & Gyn., (1987).
Brundin, J., Transcervical sterilization in the human female by hysteroscopic application of hydrogelic occlusive devices into the intramural parts of the Fallopian tubes: 10 years experience of the P-block, European Journal of Obstetrics & Gynecology and Reproductive Biology, vol. 39, pp. 41-49, 1991.
Complete Chinese-to-English translation of Chinese Patent Publication No. CN 1047447A.
Conceptus Annual Report (1995) pp. 3, 5, 7, 9, 13-14 and 22.
Conceptus Annual Report (1996) pp. x, 3, 9 and 13-14.
Erb, R.A. et al. "Hysteroscopic Oviductal Blocking with Formed-in-Place Silicone Rubber Plugs," The Journal of Reproductive Medicine, pp. 65-68, Aug. 1979.
European Search Report for Application No. EP 05 00 6090 dated Jun. 7, 2005 (3 pages total).
Fischer, Michael E. et al., "Silicone Devices for Tubal Occlusion: Radiographic Description and Evaluation," Radiology (Jun. 1984).

Free, Michael J. et al., "Technology for Mechanical Fallopian Tube-Blocking Device," Advances in Female Sterilization Techniques (Harper & Row 1976).
Gordon, A.G., et al., Atlas of Gynecologic Endoscopy, Mosby-Wolfe Press, 2nd Edition, 1995 (Title Page and Table of Contents are enclosed herewith).
Gupta, D.N. et al. "Antifertility Effect of an Intrafallopian Tubal Copper Device," Indian J. Exp. Biol., vol. 14, pp. 316-319, May 1976.
Hamou, J. et al. "Hysteroscopic Reversible Tubal Sterilazation," ACTA Europaea Fertilitatis, vol. 15, No. 2, 1984.
Hamou, J. et al., "Hysteroscopic Placement of Nylon Intratubal Devices for Potentially Reversible Sterilization," The Fallopian Tube: Basic Studies and Clinical Contributions (1986).
Hayashi, Motoyuki, "Ch. 28: Tubal Sterilization By Cornual Coagulation Under Hysteroscopy," Human Sterilization (Ralph Richart et al., eds. 1972).
Hosseinian, Abdol "31: Hysteroscopically Delivered Tubal Plugs," Reversal of Sterilization (John Sciarra et al., eds. Harper & Row 1978).
Hosseinian, et al., "Hysteroscopic Implantation of Uterotubal Junction Blocking Devices", Advances in Female Sterilization Techniques, 1976, Sciarra, et al., Eds., Harper & Row, New York, pp. 169-175.
International Preliminary Report on Patentability (Chapter 1 of the PCT), Written Opinion of the International Searching Authority, for PCT/US2004/028406, mailed Mar. 30, 2006, 7 pages.
PCT Transmittal of the International Search Report and the Written Opinion of the International Searching Authority, for PCT/US2004/028406, mailed Mar. 4, 2005, 13 pages.
J.F. Huka & K.F. Omran, "Ch. 27: Cauterization For Tubal Sterilization," Human Sterilization (Ralph Richart et al., eds. 1972).
Jay Cooper & Richard Houck, "Ch. 33: Study Protocol, Criteria, and Complications of the Silicone Plug Procedure," Female Transcervical Sterilization (Gerald Zatuchni, M.D. et al., eds., Harper & Row 1983).
Jay M. Cooper, "Hysteroscopic Sterilization," Clinical Obstetrics and Gynecology, vol. 35, No. 2 (Jun. 1992).
Leonard, Fred "Ch. 14: Polymer Implants," Female Sterilization (Ralph Richart et al., eds. 1972).
Luukkainen, Tapani et al., "15: Five Years' Experience with the Nova-T and T-Cu IUDs," Intrauterine Contraception (Gerald Zatuchni et al., 1984).
Malinak, Russell, M.D. et al., "Oviduct Occlusion Following Implanation of Proplast," Advances in Female Sterilization Techniques (John Sciarra et al., eds. Harper & Row 1976).
Manganiello, Paul D. et. al., "A Bipolar Radiofrequency Catheter Fails to Occlude a Feline Uterine Horn: A Model for Fallopian Tube Occlusion, " The Journal of the American Association of Gynecologic Laparoscopists, vol. 5, No. 3 (Aug. 1998).
Medical News, "Hysteroscope simplifies sterilization," J. of Am. Med. Assn., vol. 225, No. 6 (Aug. 6, 1973).
Neuwirth, Robert S. et al., "Hyesteroscopic Sterilization," Hysteroscopic Sterilization (John Sciarra et al. eds., 1974).
PCT European Search Report, PCT Application No. 08100783.3-2310, mailed Apr. 14, 2008, 6 pages.
Quinones, Rodolfo et al., "Tubal Electrocoagulation Under Hysteroscopic Control," Hysteroscopic Sterilization (John Sciarra et al., eds. 1973).
Reed, T.P., et al., "Tubal Occlusion with Silicone Rubber," The Journal of Reproductive Medicine, pp. 25-28, Jul. 1980.
Richard Houck & Jay Cooper, "Hysteroscopic Tubal Occlusion With Formed-InPlace Silicone Plugs: A Clinical Review," Obst. & Gyn., vol. 62, No. 5 (Nov. 1983).
Robert Neuwirth, Richard Levine, and Ralph Richart, "Hysteroscopic tubal sterilization," Am. J. of Obst. And Gyn., vol. 116, No. 1 (May 1, 1973).
Ross, P.L. et al., "Transcatherether Tubal Sterilizaiton in Rabbits," Investigative Radiology, vol. 29, No. 5, pp. 570-573, 1994.
Sciarra, J.J., et al., eds., Advances in Female Sterilazation Techniques, Harper & Row, Publishers, 1976, Title page and Table of Contents are enclosed herewith, pp. 169-181, 186-189.

Schmitz-Rode, Thomas et. al., "Experimental Nonsurgical Female Sterilization: Transcervical Implantation of Microspindles in Fallopian Tubes," Journal of Vascular and Interventional Radiology, vol. 5, No. 6 (Nov.-Dec. 1994).

Sciarra, John "26: Hysteroscopic Approaches for Tubal Closure," Fertility and Sterility: Official J of the Am. Fertility Soc., vol. 34, No. 5 & 6 (1980).

Steptoe, P.C., "The Potential Use of Intratubal Stents for Reversible Sterilaztion," *Laaroscopy*, pges. 91-99, circa 1976.

Sugimoto, Osamu, "Hysteroscopic Sterilization by Electrocoagulation," Hysteroscopic Sterilization (John Sciarra et al., eds., 1973.

Swope, C.H. "Ch. 23: Production Of Clinically Useful Interactions of Laser Radiation With Tissue," Human Sterilization (Ralph Richart et al., eds. 1972).

Theodore Reed & Robert Erb, "Hysteroscopic Tubal Occlusion With Silicone Rubber," Obst. & Gyn., vol. 61, No. 3 (1983).

Thompson, Horace et al., "Evaluation of Experimental Methods of Occluding the Uterotubal Junction," Female Sterilization: Prognosis For Simplified Outpatient Procedures (Gordon Duncan et al, eds. 1972).

U.S. District Court California Northern District, Case #09-cv-02280 WHA, Hologic Inc.'s First Amended Invalidity Contentions, Jan. 22, 2010, 31 pages.

U.S. District Court California Northern District, Case #09-cv-02280 WHA, Hologic Inc.'s Invalidity Contentions, Jan. 4, 2010, 70 pages.

V. Rimkus & K. Semm, "Hysteroscopic Sterilization—a Routine Method?" Int'l. J. Fertility vol. 22 (1977).

Zipper, J. et al., "Supression of fertility by intrauterine copper and zine in rabbits," Am. J. of Obstetrics and Gynecology (Oct. 15, 1969).

\* cited by examiner

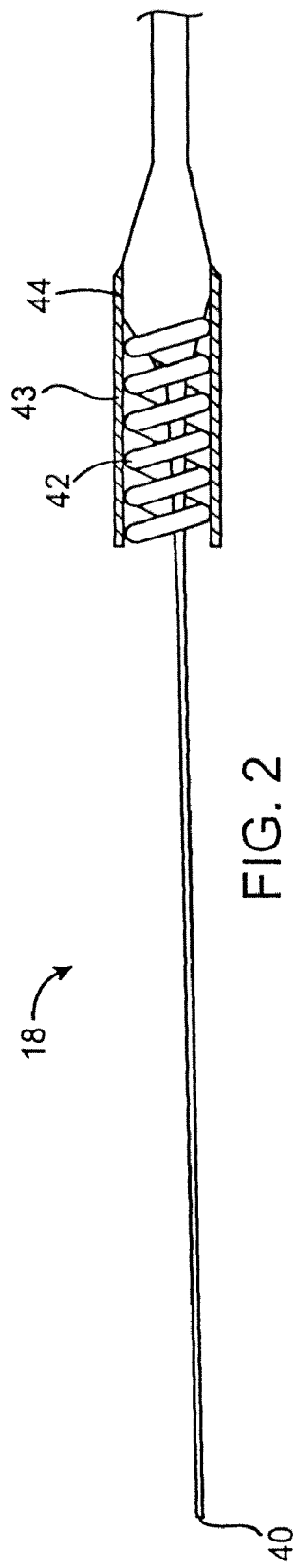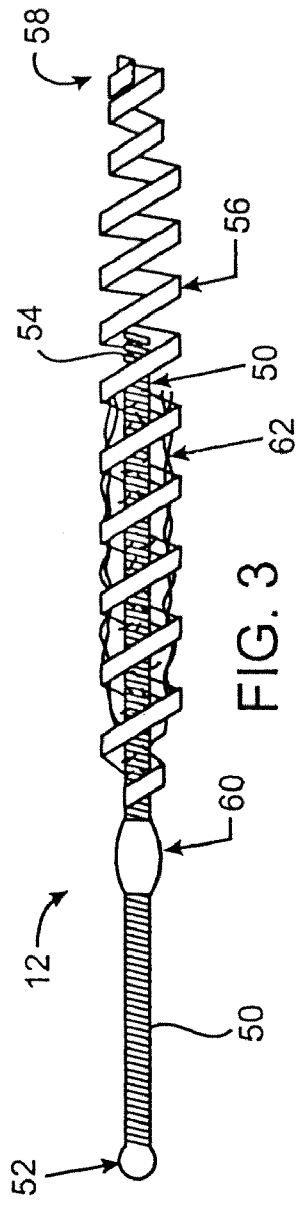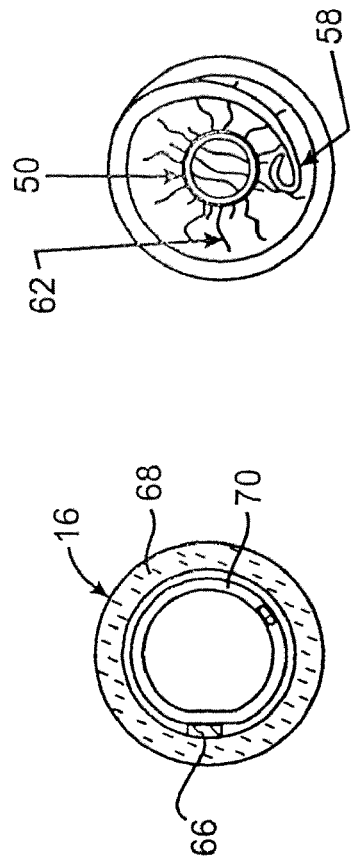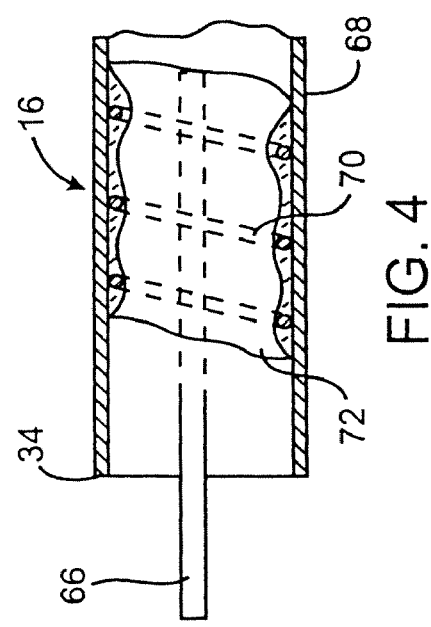

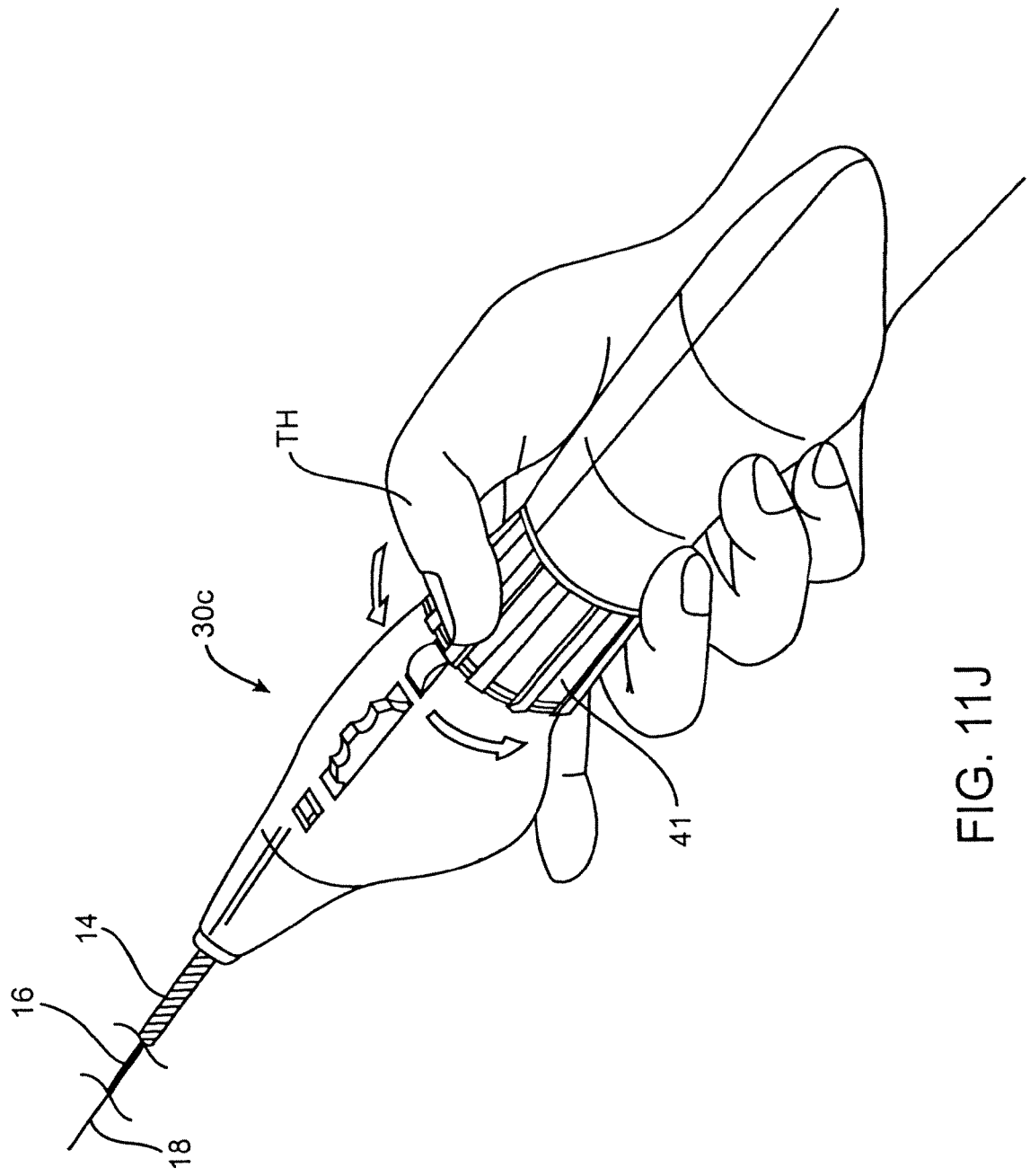

DEPLOYMENT ACTUATION SYSTEM FOR INTRAFALLOPIAN CONTRACEPTION

CROSS-REFERENCES TO RELATED APPLICATIONS

This application is a continuation of and claims the benefit of the filing date of U.S. patent application Ser. No. 12/506,953 filed Jul. 21, 2009, now U.S. Pat. No. 7,934,504 which is a continuation of and claims the benefit of the filing date of U.S. patent application Ser. No. 11/154,144 filed Jun. 15, 2005, now issued as U.S. Pat. No. 7,591,268, which is a continuation of and claims the benefit of the filing date of U.S. patent application Ser. No. 10/785,553 filed Feb. 23, 2004, now issued as U.S. Pat. No. 7,506,650, which is a continuation of and claims the benefit of the filing date of the U.S. patent application Ser. No. 09/644,287, filed on Aug. 22, 2000, now issued as U.S. Pat. No. 6,709,667, which claims the benefit of priority from U.S. Provisional Application Ser. No. 60/150,238 filed on Aug. 23, 1999, and is related to U.S. patent application Ser. No. 09/644,277, now issued as U.S. Pat. No. 6,763,833 entitled "Insertion/Deployment Catheter System for Intrafallopian Contraception", which was filed concurrently therewith, the full disclosures of which are all incorporated herein by reference.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The present invention generally relates to medical devices, systems, and methods. In a particular embodiment, the invention provides temporary or permanent intrafallopian contraceptive devices, delivery systems, and non-surgical methods for their deployment.

While the theoretical effectiveness of existing non-surgical contraceptive techniques, including barrier methods and hormonal therapies, is well established, the actual effectiveness of most known methods is disappointing. One reason for these disappointing results is that many of the presently available methods for inhibiting pregnancy without surgery depend upon significant user involvement. Non-compliance typically results in quite high rates of failure, and overcoming user non-compliance to improve overall efficacy has proven quite difficult.

One form of long term contraception which is less susceptible to user non-compliance is the intrauterine device (IUD). IUDs have been found to have higher rates of reliability, and are effective for a longer period of time, then most other commercially available contraceptives. Unfortunately, IUDs are also associated with serious infectious complications. For this reason, the use of IUDs within the United States has decreased dramatically. Additionally, IUDs are subject to unplanned expulsion, and are removed due to excessive pain or bleeding in a significant percentage of cases, further reducing acceptance of the IUD as a method of inhibiting pregnancy.

Commercially available options for permanent sterilization include fallopian tube ligation and vasectomy. These methods are surgical and are not available to many people in the world. It is common knowledge that fertilization occurs in the fallopian tubes where the sperm and ovum meet. Tubal ligation avoids this by surgical and complete occlusion of the fallopian tubes.

In work done in connection with the present invention, it has previously been proposed to transcervically introduce a resilient coil into a fallopian tube so as to inhibit conception. PCT Patent Application No. 99/15116, assigned to the present assignee (the full disclosure of which is incorporated herein by reference) describes devices which are transcervically inserted into a tubal ostium and mechanically anchored within the fallopian tube. The described devices may promote a tissue ingrowth network to provide long term conception and/or permanent sterilization without the need for surgical procedures, and should avoid the risks of increased bleeding, pain, and infection associated with intrauterine devices.

While the recently proposed intrafallopian contraceptive devices represent a significant advancement in the art, still further improvements would be desirable. In general, it would be desirable to provide improved non-surgical devices, systems, and methods for inhibiting pregnancy. It would be beneficial if these improved techniques increased the ease, speed, and reliability with which these contraceptive devices could be deployed. It would be further beneficial if these improved access and deployment techniques could safely and effectively be performed without numerous assistants, and if they did not require expensive medical equipment so that they could be implemented by health care professionals in an outpatient clinic. Some or all of these advantages are provided by the device described hereinbelow.

SUMMARY OF THE INVENTION

The present invention generally provides improved medical devices, systems, and methods. The techniques of the present invention are particularly useful for improving the ease, speed, and reliability with which contraceptive devices can be deployed transcervically into an ostium of a fallopian tube. The invention generally provides intrafallopian contraceptive systems having a handle adapted for manipulation and actuation by a single hand of a healthcare provider. Typically, the handle includes at least one actuator which can be manipulated by the same hand used to grip the handle. In many embodiments, the healthcare provider can advance the contraceptive device into an ostium of a fallopian tube by manipulating the handle, can withdraw a sheath from around the contraceptive device, can expand the contraceptive device from a small profile configuration to a large profile configuration, and/or can detach the expanded contraceptive device from the remaining components of the contraceptive system, ideally all with one hand. Advantageously, this leaves the other hand free to grasp and manipulate a hysteroscope, allowing the healthcare provider to orient the system toward the tubal ostium and effect its deployment while optically viewing and verifying the deployment, rather than relying on coordinating the efforts of two separate individuals to access the target site and deploy the contraceptive device. Deployment may, alternatively, be directed under a variety of imaging modalities, including ultrasound, fluoroscopy, or possibly even with tactile guidance. Mechanically coupling the various elongate deployment components to a common proximal housing can also avoid confusion over which component is to be moved, and which is to be maintained at a fixed position.

Hence, the invention facilitates deployment of intrafallopian contraceptive devices in a wide variety of healthcare settings.

In a first aspect, the invention provides a contraceptive delivery system comprising a contraceptive device expandable from a small profile configuration to a large profile configuration. The contraceptive device in the small configuration is insertable into an ostium of a fallopian tube. A first elongate body has a proximal end and a distal end with a receptacle disposed adjacent the distal end. The receptacle releasably receives the contraceptive device. A proximal handle is disposed at the proximal end of the first elongate body. The handle has a size and shape suitable for gripping with a single hand. At least one actuator is mounted on the handle. The actuator is moveable by the hand while the hand grips the handle so as to expand the contraceptive device to the large profile configuration and affix the contraceptive device within the ostium of the fallopian tube.

Preferably, the contraceptive delivery system will further include a sheath having a lumen that slidably receives the receptacle so that movement of the at least one actuator withdraws the sheath proximally from the contraceptive device. This arrangement allows the healthcare provider to maintain the position of the contraceptive device by holding the handle at a fixed position with the same hand that is used to move the actuator. This leaves the other hand free to support the hysteroscope, which will often be used to optically direct the deployment procedure.

The system will often further include means for expanding the uncovered contraceptive device after the sheath has been withdrawn. The expansion means will often be coupled to the contraceptive device and will be operable by the actuator. Separating at least a portion of the expansion and sheath withdrawal mechanisms can help avoid resilient expansion forces from acting against the sheath, which forces might impede movement of sheath and make it difficult to hold the contraceptive device accurately in position during deployment. While a variety of expansion means may be provided (such as inflation balloons and fluid lumens for plastically deforming a stent-like structure, or the like), the preferred expansion means comprises a second elongate body which moves relative to the first elongate body to effect expansion of the contraceptive device after the sheath is withdrawn. In the exemplary embodiment, the first and second elongate bodies restrain a resilient outer helical coil of the contraceptive device by maintaining a torque until the at least one actuator moves a second elongate body.

In some embodiments, a first movement of a dual-function actuator relative to the handle moves the sheath relative to the first elongate body without moving the second elongate body relative to the first elongate body. A second movement of the dual-function actuator after the first movement moves the second elongate body relative to the first elongate body. Optionally, a latch may releasably restrain movement of the second elongate body relative to the first elongate body. As the first elongate body will often releasably hold the contraceptive device, this can keep the device at the target location during at least a part of the deployment procedure. The first elongate body may threadingly engage the contraceptive device, and may be decoupled from the contraceptive device by rotating the handle or a decoupling actuator.

In another aspect, the invention provides a contraceptive delivery system comprising a contraceptive device which is expandable from a small profile configuration to a large profile configuration. The contraceptive device in the small configuration is insertable into an ostium of a fallopian tube. A first elongate body has a proximal end and a distal end. A receptacle is disposed adjacent the distal end of the first elongate body. The receptacle releasably receives the contraceptive device. A sheath has a lumen which slidably receives at least a portion of the contraceptive device. A second elongate body extends proximally from the contraceptive device to a proximal end. A handle is disposed at the proximal end of the first elongate body. The handle has at least one actuator, and a first movement of the at least one actuator withdraws the sheath proximally from the contraceptive device. A second movement of the least one actuator moves the second elongate body relative to the first elongate body so as to expand the contraceptive device to the large profile configuration.

In yet another aspect, the invention provides a medical device comprising an elongate guiding structure having a proximal end and a distal end. The guiding structure is laterally flexible and increases in flexibility toward the distal end so that the guiding structure is suitable for distally tracking a body lumen. A proximal handle is affixed adjacent the proximal end of the guiding structure. The handle has a slot that laterally receives the guiding structure adjacent the distal end. A detent is capable of restraining the guiding structure within the slot to facilitate introducing the distal portion into a lumen.

In a method aspect, the invention comprises inserting a contraceptive device transcervically into an ostium of a fallopian tube by gripping a handle with a hand of a healthcare worker and moving the hand. The handle is coupled to the contraceptive device by an elongate body. The inserted contraceptive device is expanded by moving an actuator on the handle while the hand grips the handle. The expanded contraceptive device is detached from the elongate body so that the contraceptive device inhibits conception.

Generally, a hysteroscope is manipulated by another hand of the healthcare worker to orient the contraceptive device toward the ostium while the healthcare worker views an image of the ostium with the hysteroscope. This allows the healthcare worker to simultaneously manipulate these two components of the contraceptive delivery system, avoiding complex coordination between two individuals.

BRIEF DESCRIPTION OF THE DRAWINGS

FIG. 2 is a side view of a removable core wire of the contraceptive system of FIG. 1B.

FIG. 3 is a contraceptive device of the contraceptive system of FIG. 1B, in which an outer helical coil is in a large profile configuration.

FIG. 3A is an end view of the contraceptive device of FIG. 3.

FIG. 4 is a side cross-section of a distal end of a delivery catheter of the contraceptive system of FIG. 1B.

FIG. 4A is an axial cross-sectional view of the delivery catheter of FIG. 4.

FIGS. 11A through 11K schematically illustrate a method for deploying a contraceptive device using the system of FIG. 1B.

DESCRIPTION OF THE SPECIFIC EMBODIMENTS

The present invention provides a contraceptive device, system, and method which can be used to inhibit pregnancy, typically for the long-term inhibition of pregnancy, and often providing permanent contraception or sterilization. By introducing at least a portion of these contraceptive devices into an ostium of a fallopian tube, the risks of unplanned expulsion, pelvic pain, and infectious complications may be significantly reduced. Although the present invention may be included within a group of contraceptive techniques generally referred to as fallopian tube occlusion methods, the invention need not be advanced fully into the fallopian tube, and in some embodiments, need not fully block the tubal lumen to effectively disrupt fertilization. As described in co-pending International Patent Application No. 99/15116, assigned to the present assignee (the full disclosure of which is incorporated herein by reference), contraception may optionally be provided by fully occluding the tubal lumen, and/or by sufficiently disrupting the fertilization process without total occlusion. In some embodiments, including a bioactive material such as copper may enhance the devices effectiveness.

As used herein, a structure is inserted "within a tubal ostium" whenever the structure is advanced from the uterus into (and optionally beyond) the tubal ostium into the uterotubal junction and/or the fallopian tubes.

Figure 1:
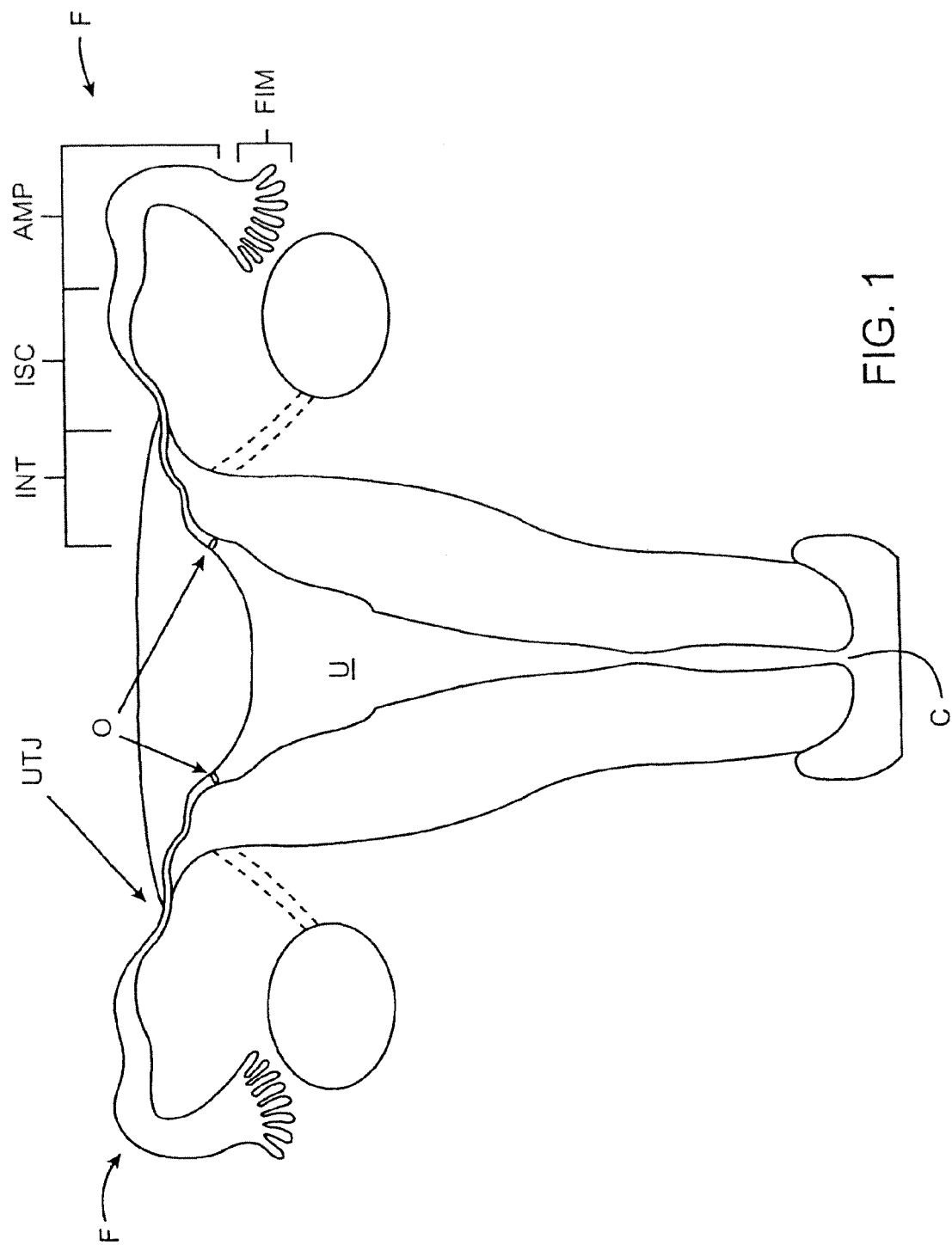
FIG. 1 illustrates the uterine and tubal anatomy for deployment of the contraceptive devices of the present invention.

Referring now to FIG. 1, access to uterus U will generally be gained through cervix C. From within uterus U, fallopian tubes F are accessed via tubal ostiums O.

Fallopian tubes F generally include three segments between ostium O and the fimbria FIM. Beginning adjacent uterus U, the intramural segment INT of fallopian tubes F are surrounded by the muscular uterine tissues. Beginning at uterotubal junction UTJ, fallopian tubes F extend beyond the uterine tissues and within the peritoneal cavity along an isthmic segment ISC, and then along an ampullary segment AMP.

In general, the ideal placement for the intrafallopian contraceptive devices of the present invention is spanning the intramural INT to isthmic ISC portion of the fallopian tube. Where a radially expandable attachment mechanism such as an outer coil is included on the intrafallopian contraceptive device, that expandable or anchoring structure will preferably span the uterotubal junction UTJ. It should be noted that the uterotubal junction UTJ may be defined as the plane where the fallopian tube meets the peritoneal cavity. It should also be noted that the narrowest portion of the fallopian tube need not necessarily be disposed in the isthmic segment ISC, particularly once the contraceptive fallopian device (often having a radially expandable anchoring structure) is deployed therein. In fact, work in connection with the present invention has shown that the effectively narrowest portion of the tube may be at or adjacent the uterotubal junction UTJ.

Figure 1A:
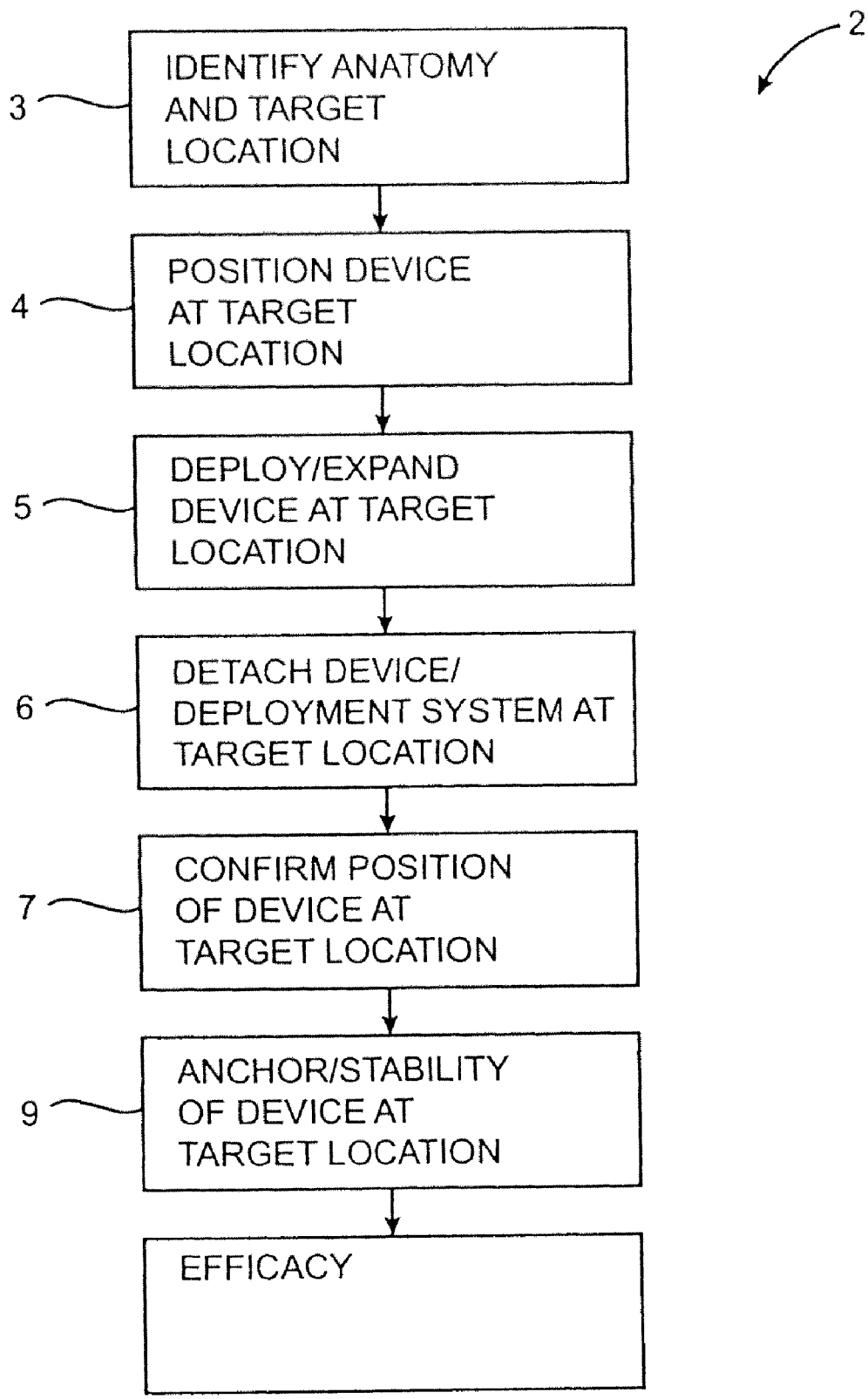
FIG. 1A schematically illustrates method steps for an exemplary contraceptive device deployment method.

Referring now to FIG. 1A, an overview of an exemplary method 2 for deploying and using the contraceptive devices of the present invention is helpful to understand the selection of structures used in those devices. It should be understood that not all steps need be performed in every deployment. Nonetheless, reviewing the exemplary deployment method 2 will help to understand the structures described hereinbelow.

Identification of the anatomy and target location 3 allows the operator to determine the preferred placement of the contraceptive device within the ostium, and also to determine if any special circumstances are present for a particular device placement procedure. Anatomy and target location identification can be facilitated using a variety of known visualization modes, including hysteroscopy, sonography (ultrasound), fluoroscopy, and the like. Hence, an exemplary contraceptive device may be adapted to delivery using more than one imaging modality.

The exemplary contraceptive device will also preferably be able to accommodate a wide variety of anatomies. Two factors contribute to the importance of this variability: First, a wide variation may be observed between tubal anatomies of differing patients. Secondly, it can be quite difficult to determine and identify the specific tubal anatomy of a particular patient. As a result, the preferred contraceptive device may incorporate safeguards allowing sufficiently accurate placement (with tolerance for normal operator error), as well as for the variance in the length and diameter of the various segments of the fallopian tube.

Exemplary deployment method 2 in FIG. 1A will also include positioning of the device at the target location 4. Once again, a wide variety of techniques might be used to assist a healthcare professional in positioning the device in the correct location, including visualization techniques, providing high-contrast markers (such as radiopaque markers, echogenic markers, or the like), providing tactile indication of the placement position by including physical stops or "bumpers" (which may be adapted to engage reference tissues in such a tactile way as to send a signal to the healthcare professional), or the like. Device positioning can be significantly facilitated by providing an appropriate device and/or deployment system design having the proper flexibility, navigation characteristics, friction reduction surfaces, small delivery profile, coatings, and the like. Once again, device positioning 4 will preferably compensate for anatomical variations, operator error, and difficulties in visualization so as to help promote accurate placement.

In the exemplary deployment method 2, the device is deployed and/or expanded at the target location in the step indicated by reference numeral 5. Optionally, the device and/or deployment system may allow visualization and/or confirmation of device expansion while expansion takes place.

Generally, the contraceptive device will be detached from its deployment system at the target location in step 6. Once again, it is helpful to provide visualization and/or confirmation of detachment, which may be provided visually, via ultrasound, fluoroscopy, or the like. It should be understood that a wide variety of detachment mechanisms might be used to decouple the device from the deployment system.

In the exemplary method, it should be possible to confirm the position of the device at the target location 7. Confirmation may be provided, once again, by visualizing at least a portion of the device after detachment, often using the same visualization modality used during placement. In addition to optical visualization techniques, this may be provided by including radiopaque markers for fluoroscopic placement confirmation, sonographic markers for ultrasound placement confirmation, or the like. Optionally, specific marker locations may be provided along the contraceptive device 2, for example, to indicate the specific locations of proximal and/or distal ends of the device.

Exemplary method 2 further includes a step 9 for anchoring and stability of the device at the target location. Aspects of this step include accommodating visualization of the device so as to monitor it's stability. Anchoring of the device at the target location may include anchoring on an acute basis (such as using an expanded helical coil that can adjust and adapt to variations in the tubal lumen, an expanded stent-like structure, expanded braid, or the like) and long-term (such as may be provided by including a fiber mesh or lattice which incites a tissue reaction such as ingrowth, thereby providing fibrous tissues which affix the device in place within the fallopian tube). Similarly, stability will preferably be provided for both a short-term and a long-term, typically by designing a device with the proper resiliency and shape to accommodate physiological movement without shifting. The device will preferably be wear-profile balanced to provide sufficient anchoring without inducing pain or losing its stability due to erosion for the life of the patient.

The final step indicated on the exemplary method 2 of FIG. 1A is efficacy. This may be provided by incorporating a lumen/space filling design that sufficiently alters the function and architecture of the fallopian tube so as to inhibit conception. This may include the use of polyester fibers to incite the desired tissue reaction.

In general, the devices of the present invention may be adapted to incite a reaction tissue response in the fallopian tube through the presence polyester fibers, or the like. Ideally, this reaction can be classified as a highly localized, benign tissue reaction. The reaction results in the incorporation of the contraceptive device into the tubal lumen tissues, so that the device is firmly embedded into the surrounding tissue structure. This reaction can typically be characterized by the proliferation of smooth muscle cells and associated fibrosis. Additionally, the tubal lumen will generally exhibit an absence of the normal tubal architecture which is generally necessary for conception. The tubal lumen may also be obstructed, occluded, and/or functionally occluded by the presence of the device and associated fibrosis sufficiently to inhibit conception. The reaction is a benign one, and there appears to be no change in anatomy or structure of the outer tubal wall beyond approximately 5 to 10 mm radially outwardly from the outer coil of the device. Similarly, normal tubal architecture will often be visible about 5 mm axially beyond the device (typically distal of the device, as the device often extends into the uterus), again indicating a very localized reaction.

Figure 1B:
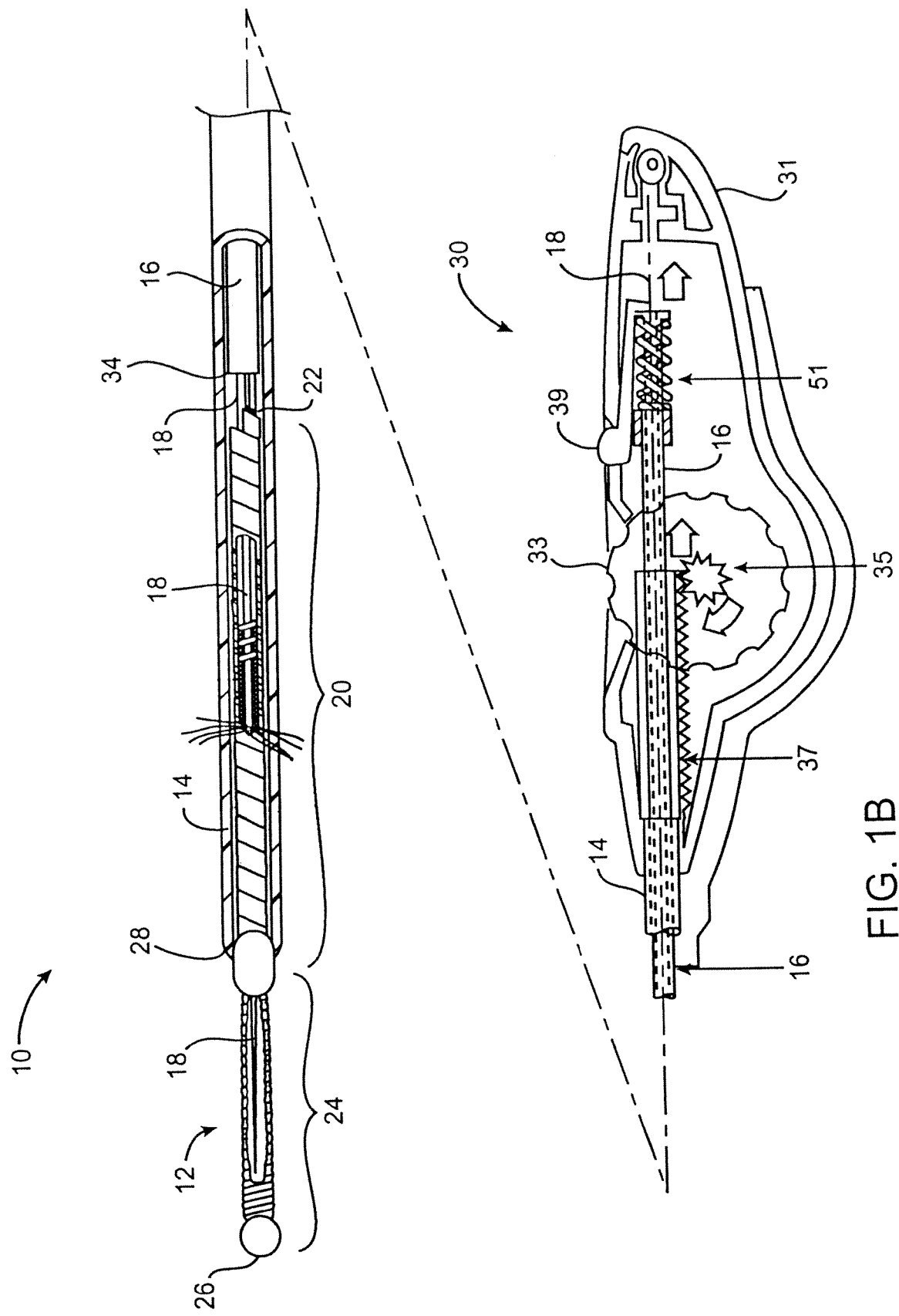
FIG. 1B is a partial cut-away side view of a contraceptive system according to the principles of the present invention.

Referring now to FIG. 1B, an exemplary contraceptive system 10 generally includes a contraceptive device 12, a sheath 14 partially surrounding the contraceptive device, a release catheter 16, and a core shaft 18. Contraceptive device 12 generally has a proximal portion 20 adjacent a proximal end 22 (disposed within sheath 14), and a distal portion 24 adjacent a distal end 26 (which are exposed beyond the distal end of sheath 14). Distal portion 24 generally functions as a distal guidewire while system 10 is advanced within the tubal ostium. Proximal portion 20 includes a radially expandable structure which can be expanded after sheath 14 is withdrawn so as to affix the contraceptive device in the deployed position.

Sheath 14 is generally a tubular structure having a distal end 28 and extending proximally to a proximal handle 30. Sheath 14 will generally have a length in a range from about 25 to about 50 cm, and will typically have an outer diameter in a range from about 0.020 to about 0.060 inches, the exemplary sheath having a length of about 39.5 cm and an outer diameter of about 0.04 inches. The inner diameter of sheath 14 may be in a range from about 0.02 inches to about 0.05 inches, with the exemplary sheath having an inner diameter of about 0.33 inches.

Release catheter 16 generally comprises a tube having a distal end 34 which releasably engages contraceptive device 12, and a proximal end coupled to housing 30 via actuator 33.

In the exemplary embodiment, core shaft 18 comprises a resilient tapering structure extending from within distal portion 24 of contraceptive device 12 proximally to handle 30. Core shaft 18 threadably engages contraceptive device 12 proximally of distal end 28 of sheath 14. In the exemplary embodiment, core shaft 18 and release catheter 16 transmit a wind-down torque onto an expandable structure of the contraceptive device so as to maintain the expandable structure in the small profile configuration. Hence, releasing core shaft 18 relative to release catheter 16 allows the expandable structure to be activated independently of movement of the surrounding sheath.

Handle 30 includes a housing 31 having a size and shape suitable for gripping with a single hand. A thumb wheel actuator 33 performs two actuation functions: first, rotation of the thumb wheel relative to housing 31 draws sheath 14 proximally by engagement between pinion 35 (attached to the thumb wheel) and rack 37 (attached to sheath 14). During this initial movement, release catheter 16 is restrained relative to housing 31 by latch 39. Once the proximal end of rack 37 engages a cooperating surface attached to release catheter 16, latch 39 can be actuated to allow release catheter 16 to move relative to the housing as the thumb wheel 33 is again turned in the direction shown. In some embodiments, spring 51 may be compressed by rotation of the thumb wheel prior to actuation of latch 39, so that actuation of the latch slides the release catheter so as to disengage the release catheter from contraceptive device 12. In this embodiment, a proximal end of core shaft 18 is affixed to the housing so that the core shaft is rotated by rotating the entire housing.

Components of housing 31 and actuators 33, 39, will generally comprise polymers, metals, or the like. The actuator mechanism may include molded and/or machined parts, and may be permanently attached to sheath 14, release catheter 16, core shaft 18, and the like so that the remaining components of the delivery system 10 are disposed of once contraceptive device 12 has been deployed. Alternatively, it may be possible to provide sterilizable, reusable, and/or responsible delivery system components if desired.

In the exemplary embodiment, housing 31 has an overall length in a range from about 2 to about 8 inches, ideally having a length of about 7.5 inches. The exemplary embodiment of rack 37 has a length of about 5.5 cm and a total travel stroke of about 4.0 cm. Release catheter 16 has a stroke of about 1 cm, and movement of the release catheter relative to core shaft 18 is inhibited prior to actuation of latch 39. Unthreading of core shaft 18 from device 12 will typically be complete in about 10 rotations or less, ideally being unthreaded with from about one quarter to about 2 full rotations of the handle (or other rotational mechanism).

While exemplary contraceptive device 12 makes use of a radially expandable helical coil to help restrain the structure during tissue ingrowth, a wide variety of mechanical and other restraint mechanisms might be included. For example, alternative mechanical anchors might be attached to the device, such as resilient coils biased to form bends, loops, and/or other secondary shapes having enhanced cross-sections, slotted tubes, Malecot-type structures, radially expandable braids, stent-like devices, and the like. The mechanical structures may be resilient, plastically deformable, or the like, and suitable structures are described in more detail in, for example, PCT Publication No. WO 99/15116.

Still further device-restraint techniques might be employed, including thermal, chemical, adhesive, and the like. These techniques can be used to avoid expulsion by increasing friction between the device and the surrounding tissues, by imposing limited tissue damage to promote scar tissue formation, and/or by promoting tissue ingrowth into the device. Thermal techniques may include, for example, transmission of electrical or laser energy along contraceptive system 10. Resistive heating of contraceptive device 10 might be effected by applying an electrical potential across the device with conductors extending along sheath 14 and release catheter 16, laser energy along an optical wave guide attached to core wire 18, or the like. Monopolar tissue desiccation might be effected via a large return electrode patch by energizing core wire 18 with radiofrequency energy, or an adhesive and/or caustic agent (such as a cyanoacrylate or silver nitrate) might be introduced via any of the lumens of the delivery system, via a dedicated lumen or structure, or the like. Biodegradable plugs and the like might also be included, and the retained structure may optionally comprise copper or other bioactive agents to help inhibit conception.

Tissue reaction to the retained contraceptive device 12 can help to provide long term contraception and/or sterilization. To promote conception inhibiting tissue reaction, device 12 will often include a tissue reaction material, the material often comprising fibers. The fibers may comprise a polyester, such as Dacron® polyesters, silk, nylon, or the like. The fibers may be in the form of a weave, a knit, a braid, a felt, or the like, or may comprise stands attached to the device body.

The components of contraceptive system 10 can be further understood with reference to FIGS. 2 through 5, in which these components are illustrated individually. Beginning with FIG. 2, core shaft 18 tapers to a gradually increasing diameter proximally of distal end 40 so as to provide increasing support of distal portion 24, proximal portion 20, and the catheter structures proximal of contraceptive device 12. This increasing support (and the associated increase in column strength) enhances the pushability of the contraceptive system while accessing the target deployment site. Threads 42 threadingly engage a coil of the contraceptive device, and are generally formed by affixing a coil with separated windings to a central core wire at a bond 44. A tube 43 may also be affixed at bond 44 to prevent binding and/or jumping of the cooperating threads, the tube ideally comprising stainless steel, platinum, or the like. In the exemplary device, core shaft 18 comprises a high strength metallic structure.

The exemplary contraceptive device 12 is illustrated in more detail in FIG. 3. Contraceptive device 12 includes a primary coil 50 which extends from a distal ball tip 52 to proximal threads 54, which may conveniently be formed by separating the proximal windings of the primary coil. The expandable structure, here in the form of a helical outer coil 56, has a proximal end bent to form a wind-down attachment 58, and has a distal end affixed to coil 50 at coil bond 60. Fiber 62 extends between the inner and outer coils, and is also disposed within primary coil 50 so as to promote tissue ingrowth throughout the cross-section of contraceptive device 12. The arrangement of coil attachment 58 and position of fiber 62 can be seen in the axial view of FIG. 3A. By making use of a contraceptive device having a distal portion 24 which can act as a guidewire, no open lumen need be provided through the center of the contraceptive device (for example, for a separate guidewire), and multiple access/deployment steps (for example, accessing the target location with a guidewire, advancing a catheter over the guidewire, removing the guidewire from the positioned catheter, and then advancing the contraceptive device) can be avoided. While the exemplary system uses threads to couple the core wire (or other deployment shaft) to the contraceptive device, a variety of alternative detachable connections might be used, including cooperating keys/slots, connectors, or the like.

In the exemplary embodiment, coil 50 is formed of a high strength resilient material, ideally comprising stainless steel wire having a diameter of about 0.005 inches, and wound to form a coil having an outer diameter of about 0.022 inches. Ball tip 52 preferably has a cross-section which is larger than the cross-section of coil 50, the ball tip generally having a diameter in a range from about 0.020 inches to about 0.050 inches, the exemplary ball tip having a diameter of 0.027 inches.

Helical coil 56 comprises a highly elastic high strength metal which is biased to expand from the low profile configuration illustrated in FIG. 1 to the larger profile configuration illustrated in FIG. 3 when released within the target site. In the exemplary embodiment, outer coil 56 comprises a ribbon of a superelastic shape memory alloy, and has a thickness of about 0.001 inches and a width of about 0.015 inches, with the ribbon being biased to form a helical coil having an outer diameter of about 0.080 inches and a length of about 3.5 cm when not otherwise restrained. Outer coil 56 is preferably fixed to primary coil 50 by a bond 60 of solder. Bond 60 will preferably be separated from ball tip 52 by a distance in a range from about 0.3 cm to about 1.0 cm. Advantageously, bond 60 may be aligned with the distal end 28 of sheath 14 so as to help present an atraumatic increase in diameter between distal portion 24 of contraceptive device 12 and the sheathed proximal portion 20 prior to deployment.

Fiber 62 may comprise a polyester, or the like. The fiber may be loosely woven or matted strands, with at least one end of the fibers affixed to primary coil 50 or outer coil 56.

Generally, the expandable structure will at least help hold contraceptive device 12 in place until tissue ingrowth occurs sufficiently so as to permanently retain the contraceptive device. Hence, the expandable structure will often benefit from a relatively high friction outer surface. Such an outer surface might make it difficult to advance the contraceptive device into position if the device is advanced without sheath 14.

Work in connection with the present invention has shown that resiliently expandable structures which have sufficient strength to reliably hold the contraceptive device within the ostium of the fallopian tube may impose significant frictional forces against a surrounding sheath. These frictional forces can significantly complicate the accurate delivery of contraceptive device. Hence, outer coil 56 is preferably maintained in a small profile configuration within sheath 14 by applying a wind-down torque between core wire 18 and release catheter 16. The core wire can transfer the wind-down torque to outer coil 16 through cooperating threads 42, 54, with the direction of the wind-down torque preferably being arranged so that the wind-down torque discourages decoupling of the threads. In other words, rotation of core wire 18 relative to contraceptive device 12 in a direction opposed to the wind-down torque is used to detach core wire 18 from contraceptive device 12.

Figure 3B:
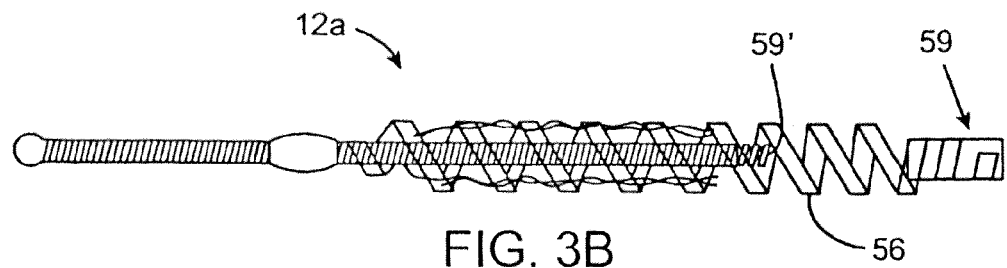
FIG. 3B illustrates a contraceptive device having a tubular band for smoothly disengaging a release pin of a release catheter.

A slight variation upon the wind-down attachment is illustrated in FIG. 3B. An alternative contraceptive device 12*a* includes a small tube or band 59 soldered within a small diameter proximal section of the outer coil 56. Band 59 can have a relatively large interface area with coil 56 to facilitate bonding. Use of the band helps avoid stress concentrations, and also presents a smooth inner lumen which may inhibit binding of the release catheter. Band 59 may comprise stainless or platinum, ideally having an inner diameter of about 0.023 inches and an outer diameter, with a thickness of the surrounding outer coil and solder bond, of about 0.030 inches. A similar band 59' may be disposed within threads 54 of coil 50 to provide a radiopaque marker, and to inhibit thread jump. Band 59' may be similar in structure to band 59, but shorter in length. Still further alternative attachment mechanisms are possible. For example, a mass or knob may be formed at the proximal end of outer coil 56 from a simple ball of solder, coil material, bend, or the like. This mass may be slidably receivable within slot of the delivery catheter.

The distal structure of release catheter 16 is shown in FIGS. 4 and 4A. The wind-down torque is releasably transferred between outer coil 56 and release catheter 16 by cooperation between bend 58 and pin 66 at the distal end 34 of the release catheter 16. Release catheter 16 generally includes a tubular body 68 formed of rigid polymers such as polyimide. Pin 66 is disposed within a lumen of tubular body 68, and is supported within the tubular body by a helical support coil 70 and adhesive 72. Interestingly, the tubular body dimensions may be driven by the wind-down torque transferred proximally by release catheter 16.

Figures 5A, 5C, 5E:
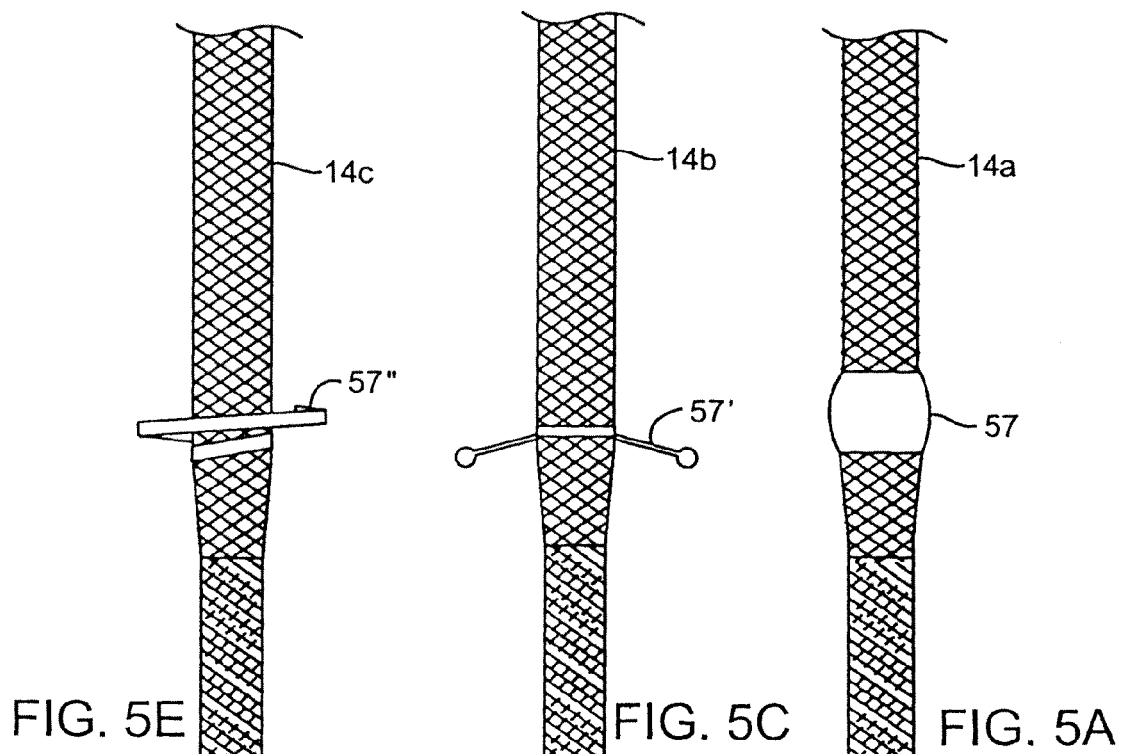
FIGS. 5A-5F illustrate sheaths having positioning surfaces for axially positioning the contraceptive device relative to the tubal ostium.
Figures 5B, 5D, 5F:
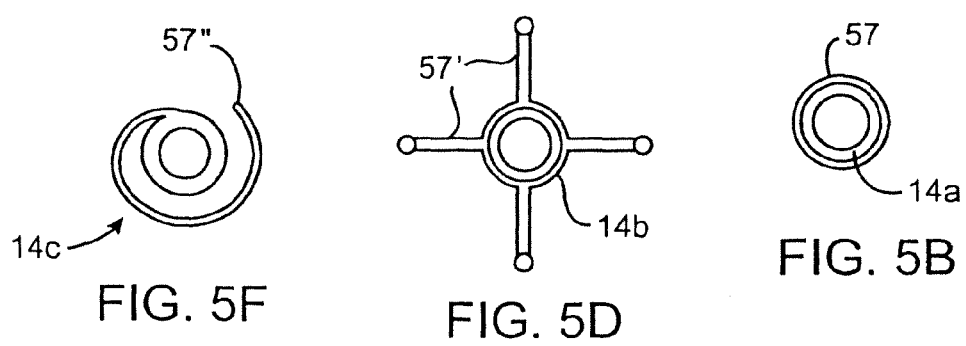
Figure 5:
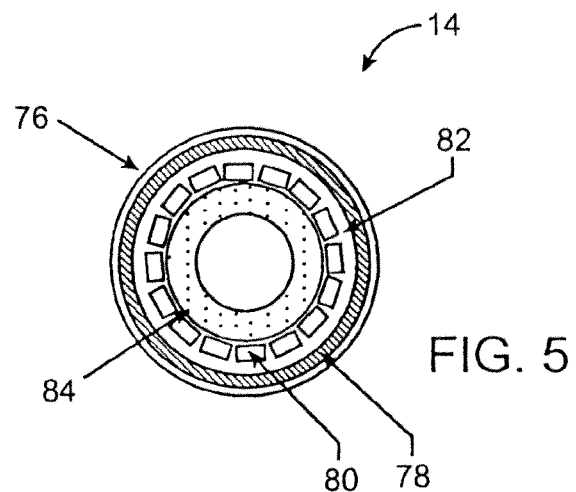
FIG. 5 is a side cross-sectional view of an outer sheath of the delivery system of FIG. 1B.

The structure of sheath 14 is illustrated in more detail in FIG. 5. Distal end 28 (see FIG. 5A) of sheath 14 will preferably be rounded, with the distal end ideally cooperating with coil bond 60 of contraceptive device 12 so as to avoid friction and facilitate distal navigation of delivery system 16 through the uterotubal junction and into the fallopian tube. The rounded distal end 28 may optionally be rounded along both the inner and outer diameter of sheath 14, or may primarily be rounded along the outer diameter so as to taper inwardly distally.

Sheath 14 will preferably have a multi-layer structure, with the layers comprising (beginning at the outside) a hydrophilic coating 76 to reduce friction during tracking and navigation. Such hydrophilic coatings become quite slippery when exposed to fluid. Below hydrophilic coating 76 is a structural layer of a polymer 78 such as Tecoflex™ along the proximal portion of sheath 14, and a reinforcing braid 80 of a metal, ideally of stainless steel, is disposed within a layer of polyimide below polymer layer 78. Along the more distal portion of sheath 14, metal braid 82 is disposed within polymer layer 78 of Tecoflex™, or the like, and the polyimide layer is absent so as to provide enhanced flexibility. The inner lumen of sheath 14 is defined by a low friction polymer coating 84, the low friction polymer ideally comprising a PTFE such as Teflon®. Exemplary sheaths 14 may be commercially available from a variety of vendors. Suitable structures may be described in more detail in published PCT patent application WO 98/57589, the full disclosure of which is incorporated herein by reference.

As schematically illustrated in FIGS. 5A through F, alternative sheaths 14A, B, and C, include bumpers 57, 57', and 57", respectively. Bumper 57 has an outer surface extending radially from the outer surface of the underlying sheath. Although bumper 57 may optionally provide a tactile indication that the sheath 14A is advancing distally beyond the target deployment position, it does not necessarily prevent the sheath from advancing so that the bumper can enter into the tubal ostium. Bumper 57 may also provide a visible marker that hinders pushing of the sheath so that the bumper moves past the ostium. Optionally, bumper 57 may comprise a colored adhesive, or may comprise a clear adhesive with a colored band of material disposed underneath.

Alternative bumpers 57' and 57" may comprise polymer or metallic structures, ideally comprising a polyethylene or a super-elastic, shape-memory alloy. These radially expandable bumper structures can be collapsed for delivery through a working lumen of a hysteroscope, and can then expand to impede advancement of the sheath by engaging the uterine tissue adjacent to the tubal ostium.

Figure 6:
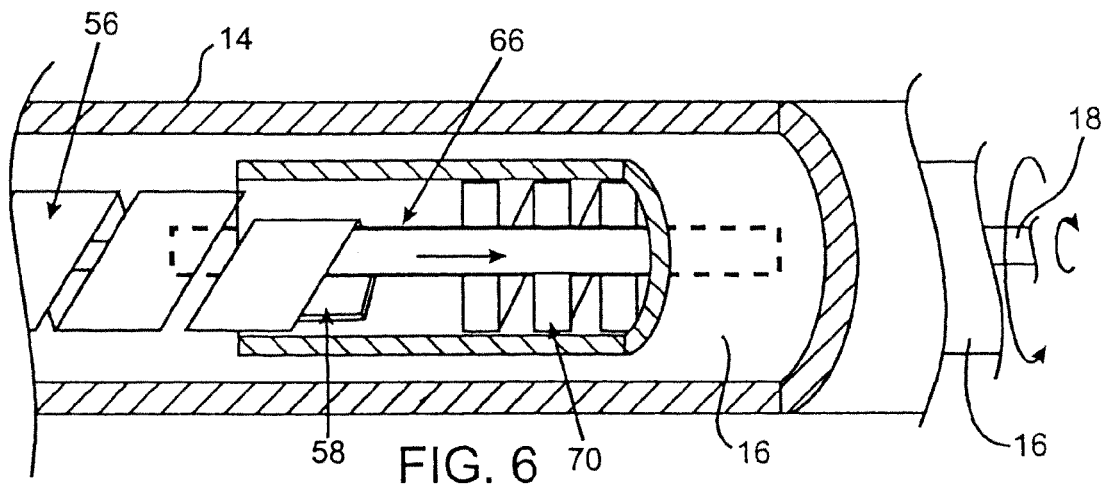
FIG. 6 is a partial cut-away view showing engagement between the outer helical coil of the contraceptive device and the release catheter so as to maintain the wind-down torque on the outer helical coil.

Referring now to FIG. 6, the sliding engagement between pin 66 of release catheter 16 and bend 58 of outer coil 56 is more clearly illustrated. FIG. 6 also shows how the wind-down torque imposed on the outer coil by the core shaft 18 and release catheter 16 help maintain the outer coil in a small profile configuration within sheath 14, allowing the sheath to be withdrawn easily. The wind-down torque can be released by sliding release catheter 16 so that pin 66 slides free of bend 58. Optionally, the release catheter may first be allowed to rotate relative to the core shaft to reduce the engagement forces between bend 58 and pin 66.

Figure 7:
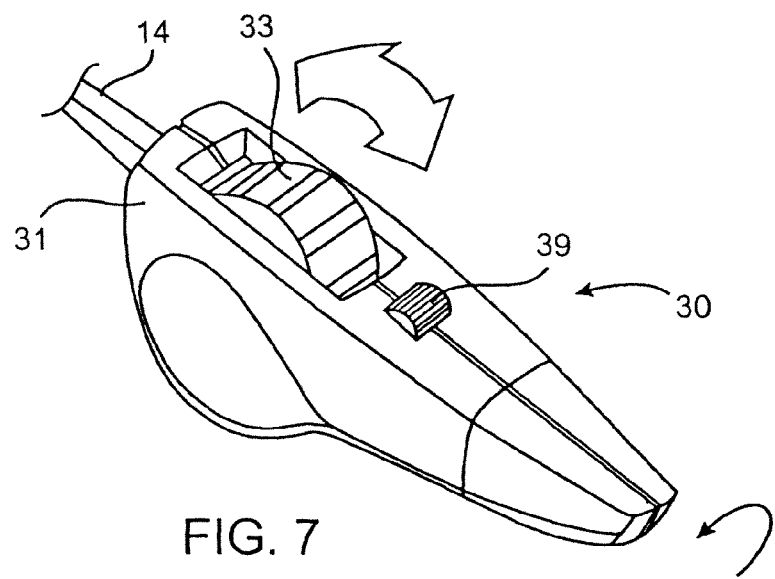
FIG. 7 is a perspective view of the proximal handle of the contraceptive system of FIG. 1B.

Referring now to FIG. 7, thumb wheel 33 and latch 39 are conveniently located for actuation by a thumb of a surgeon, nurse, or other healthcare professional while the healthcare professional grips handle 30 with the remaining fingers of the hand. This allows the healthcare professional to perform several of the deployment steps with a single hand. In general, movement of overall housing 31 is used to advance contraceptive device 12 distally into the tubal ostium, and to navigate the contraceptive delivery system within the uterotubal junction and fallopian tube. Once the contraceptive device is positioned, thumb wheel 33 withdraws sheath 14 from over the contraceptive device, while housing 31 continues to rotationally and axially couple the proximal ends of the release catheter 16 and core shaft 18, thereby maintaining the wind-down torque on the contraceptive device so as to restrain the contraceptive device in its small diameter configuration.

Once the proximal portion of the contraceptive device is exposed, latch 39 can be depressed and thumb wheel 33 can again be turned proximally to disengage pin 66 of release catheter 16 from the wound-down outer coil of the contraceptive device, thereby radially expanding the contraceptive device. Advantageously, prior to expansion, it may be possible to withdraw the contraceptive device proximally back into the sheath 14 and/or slightly reposition the contraceptive device within the tubal ostium if desired.

Once the contraceptive device has been both exposed and expanded, handle 30 is rotated as illustrated to threadingly disengage core shaft 18 from the contraceptive device 12. Hence, handle 30 allows the healthcare professional to position the contraceptive device, expose the contraceptive device, actuate the contraceptive device so as to affix the device to the surrounding tissue, and decouple the contraceptive device from the remaining components of the delivery system with a single hand.

Figure 8A:
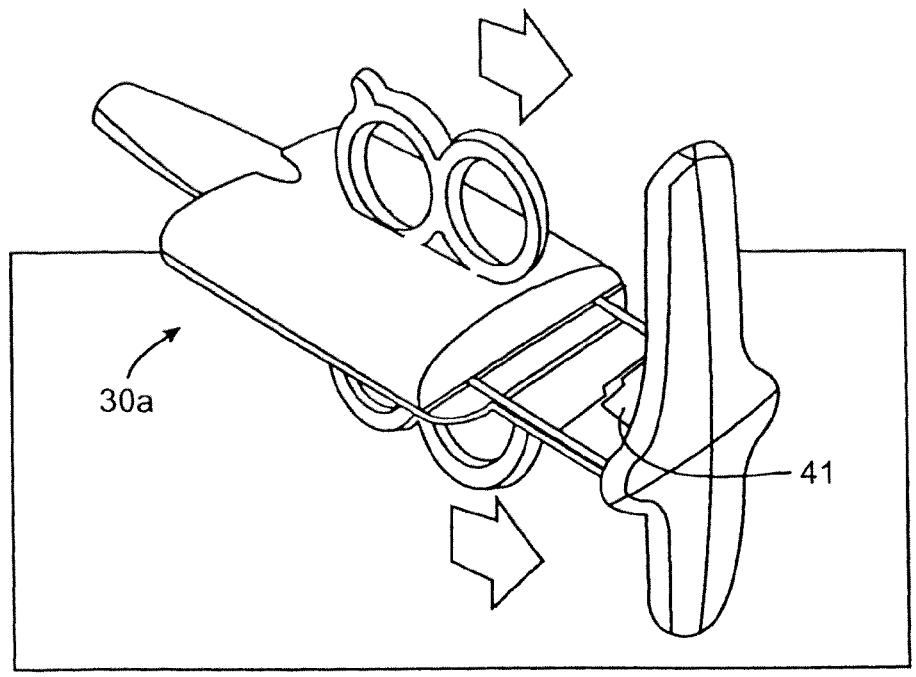
FIGS. 8A and 8B illustrate a syringe-like handle for use with the contraceptive system of FIG. 1B.
Figure 8B:
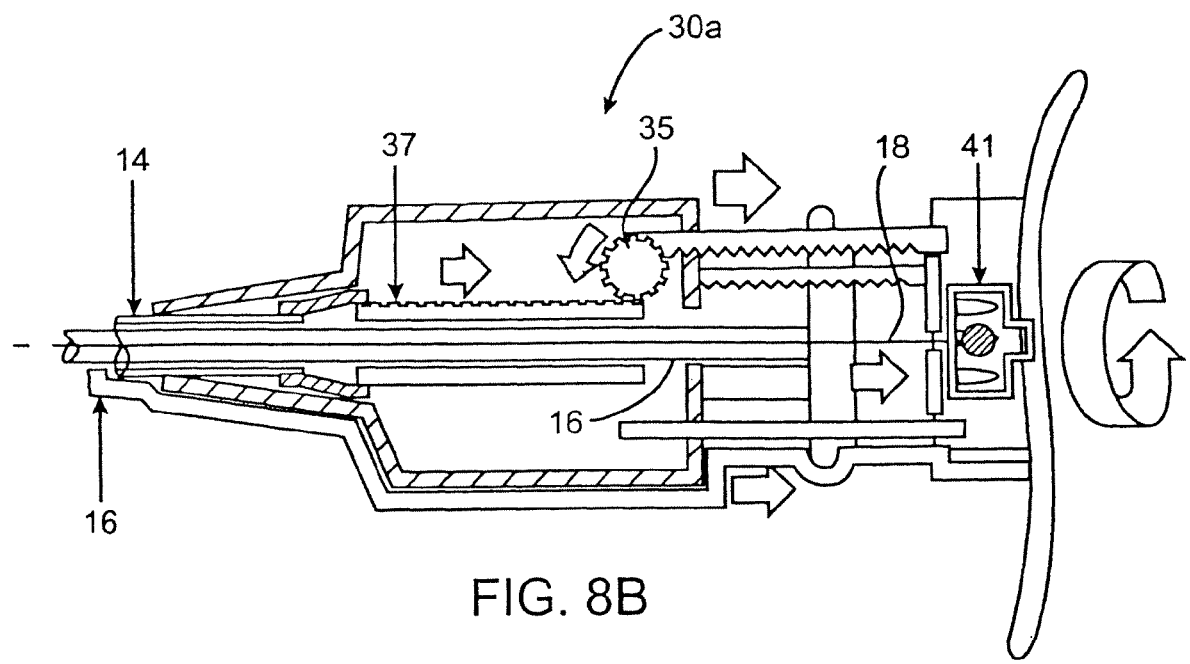

As can be understood with reference to FIGS. 8A through 11, a wide variety of alternative one-handed release handles might be used with the contraceptive delivery system of FIG. 1B. Referring now to FIGS. 8A and B, an axial motion "T" handle 30a uses a syringe-type axial pull motion to pull sheath 30 back with the fingers of a hand towards a palm of the hand (which is generally held at a fixed position). This effects axial motion of sheath 14 to withdraw the sheath from over the contraceptive device, followed by axial motion of release catheter 16 to allow the contraceptive device to expand. Optionally, a knob 41 may be affixed to the proximal end of core shaft 18, so that rotation of knob 41 threadingly disengages the core wire from the expanded contraceptive device. Knob 41 may include a releasable latch coupling the knob to the housing to prevent rotation of the core shaft and maintain the wind-down torque until release is desired. Advantageously, axial motion handle 30a allows for multiple hand sizes and various hand positions, and presents a form which is familiar to doctors.

Figure 9A:
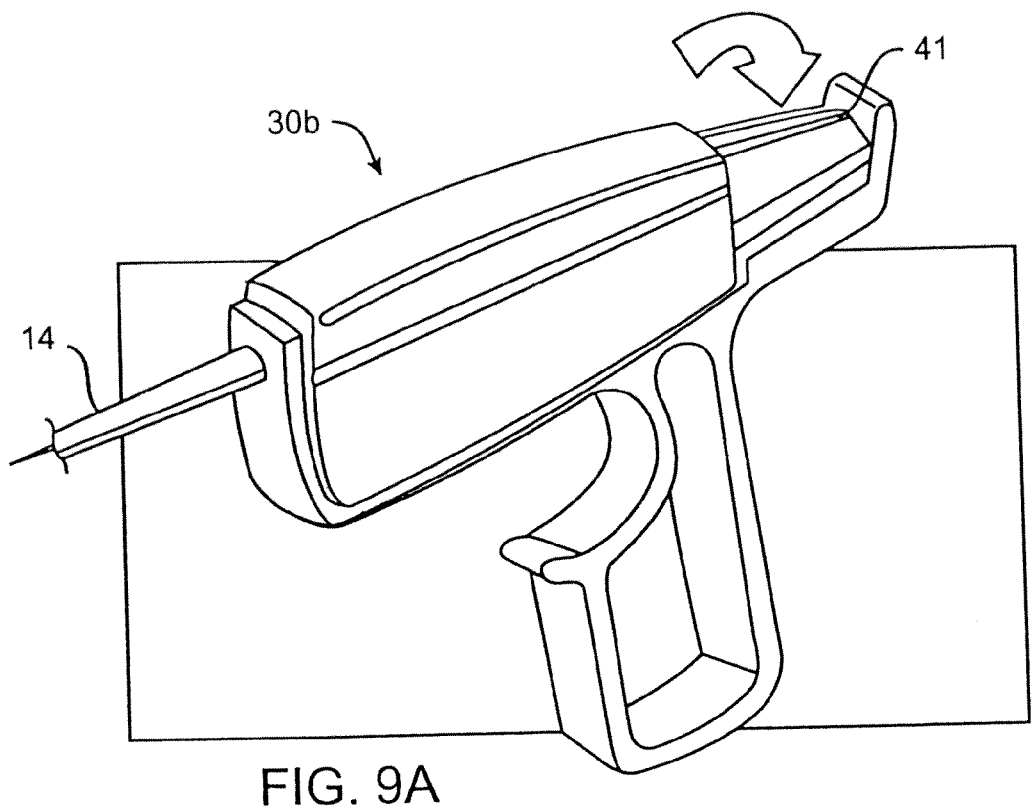
FIGS. 9A and 9B illustrate a further alternative pistol grip handle for use with the contraceptive system of FIG. 1B.
Figure 9B:
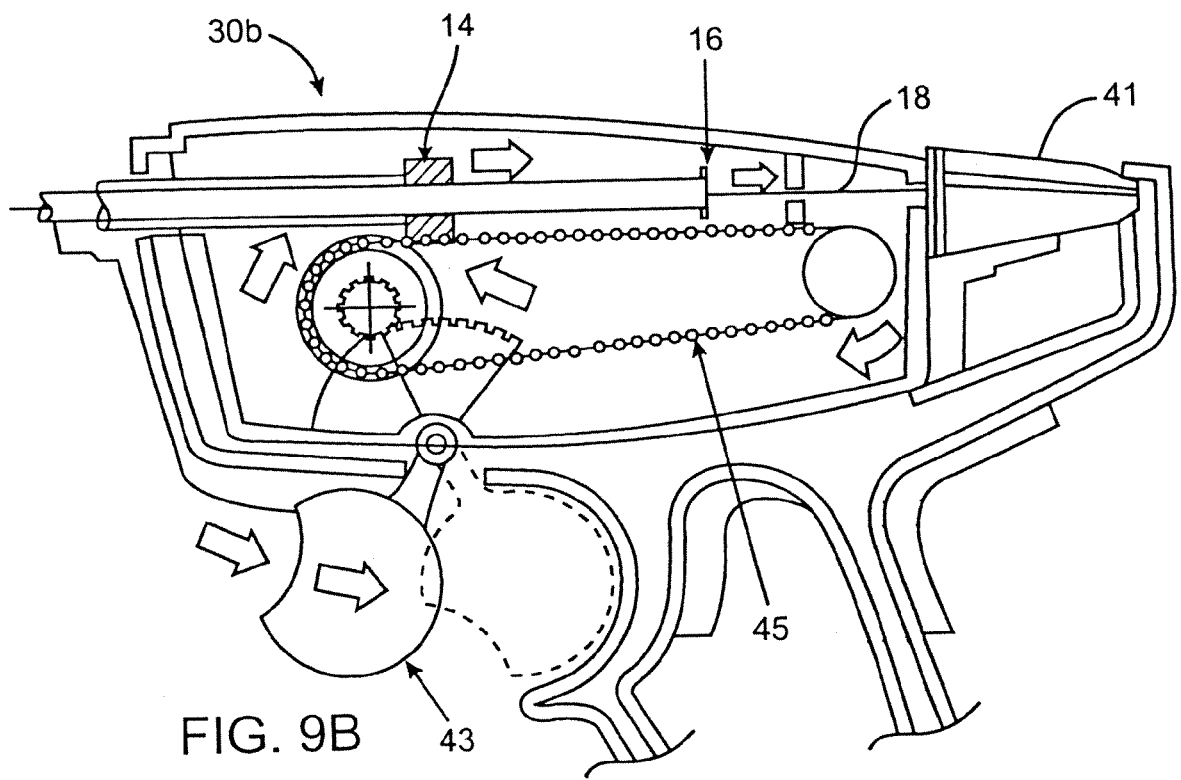

FIGS. 9A and B illustrate a still further alternative pistol grip handle 30b for effecting one-handed deployment of the contraceptive device. In this embodiment, a trigger actuator 43 moves sheath 14 and release catheter 16 via a bead chain 45 and a bead chain drive wheel and gear arrangement. After actuation of the trigger actuator 43 with, for example, and index finger of the hand, a latch button (not shown) may be depressed and knob 41 rotated by a thumb of the hand to decouple the contraceptive device from core shaft 18.

Figure 10:
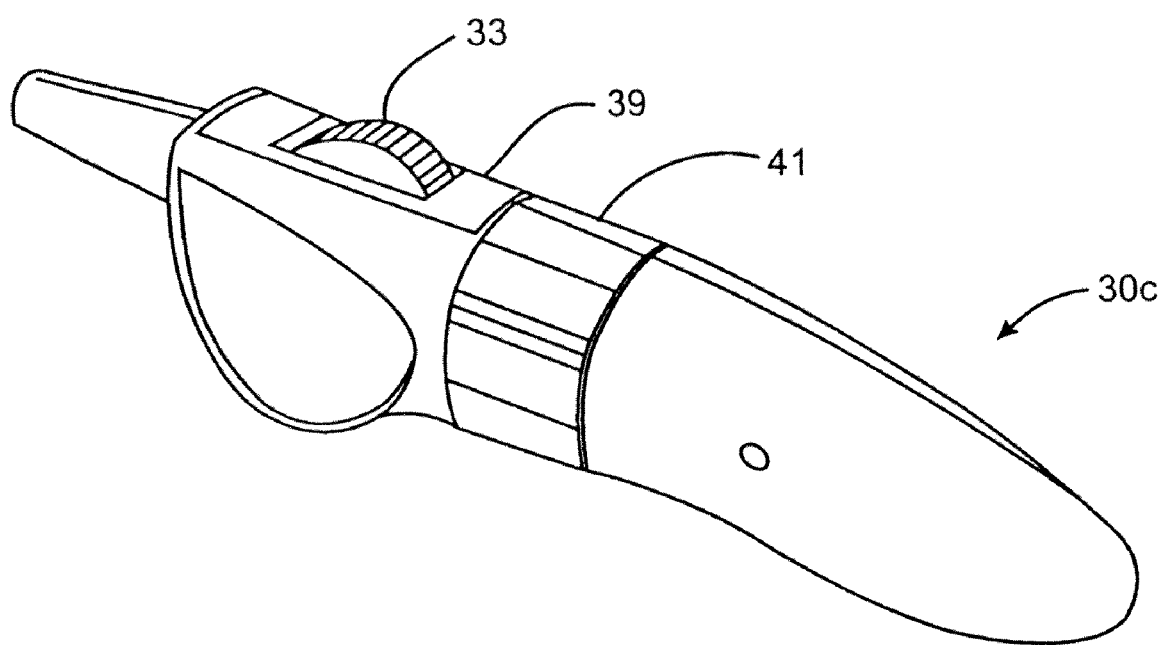
FIG. 10 is a perspective view of a preferred proximal handle of the contraceptive system of FIG. 1B having a thumb wheel, latch, and rotation knob for exposing, expanding, and releasing the contraceptive device at the target location.

Referring now to FIG. 10, a preferred one-handed release handle 30c includes a thumb wheel 33 which, when turned relative to the surrounding housing, initially causes movement of sheath 14 relative to core shaft 18 as will be described in detail herein below. Once the contraceptive device has been uncovered, depressing safety latch 39 allows the thumb wheel to again be rotated so as to move release catheter 16 relative to the core shaft to allow the contraceptive device to expand. These movements of thumb wheel 33 can easily be performed while maintaining the housing of preferred handle 30c at a fixed location, thereby avoiding movement to the contraceptive device. Once deployment has exposed and expanded the contraceptive device at the target location, knob 41 may be rotated, again while holding the remaining handle at a fixed location. The internal mechanism providing these movements is illustrated in FIGS. 11D, 11E, 11F, and 11H.

Still further alternative one-handed release handles may be provided, including an in-line slider handle 30d having a thumb slide 47 for sequential movement of the sheath 14 and then release catheter 16 relative to core shaft 18, as shown in FIG. 10. A knob 41 may be allowed to rotate relative to the housing by depressing a latch 39, or the entire housing may be rotated to detach the engagement threads, as described above.

An exemplary method for use of contraceptive system 10 can be understood with reference to FIGS. 11A through 11K. Preferably, a healthcare worker will manipulate contraceptive delivery system 10 with a first hand H1 while supporting an imaging and/or access device such as a fluoroscopy catheter, sonography catheter, or hysteroscope S with a second hand H2. This allows the healthcare professional to personally control the orientation of distal advancement of the contraceptive system and its movement and deployment while viewing the procedure through the scope S (shown here schematically by eye E). While scope S is illustrated here as a simple optical device, it should be understood that a variety of scope structures are encompassed by the system and method of the present invention, including rigid optical scopes, scopes having a coherent fiber optic bundles, scopes which include charge-couple devices (CCD's) for displaying an image of the procedure in a monitor, and the like). Exemplary hysteroscopes for use with the present invention are commercially available from Richard Wolf of Chicago, Ill. under model name 5 MM OVAL SCOPE.

Figure 11:
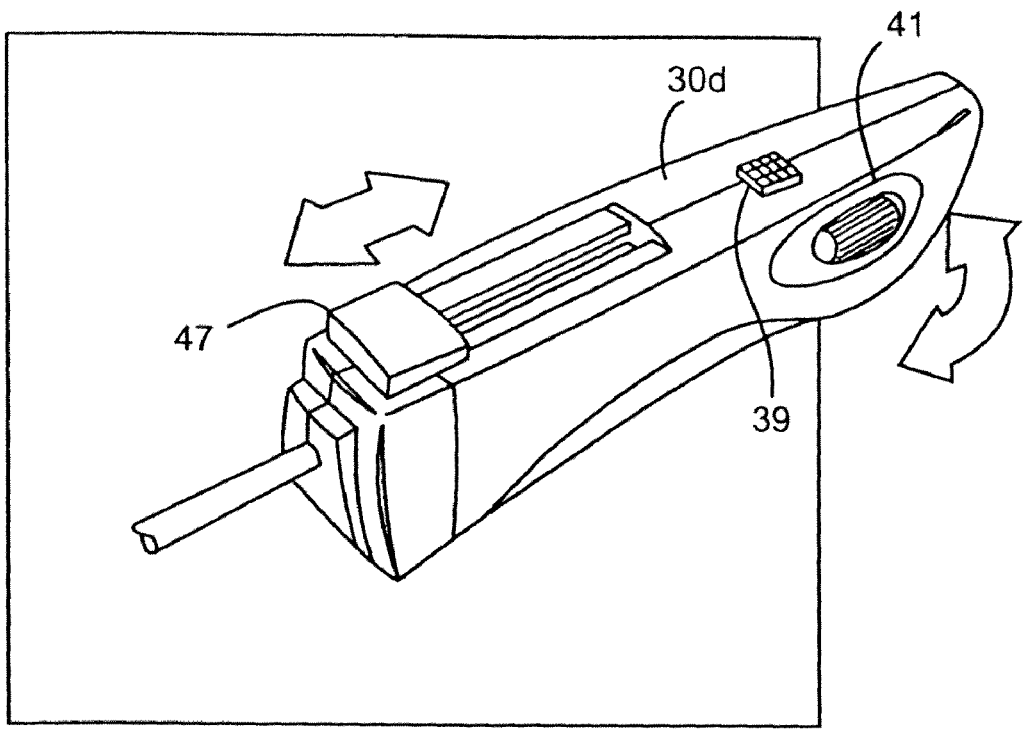
FIG. 11 is a perspective view of an alternative in-line slider handle for use with the contraceptive system of FIG. 1B.
Figure 11A:
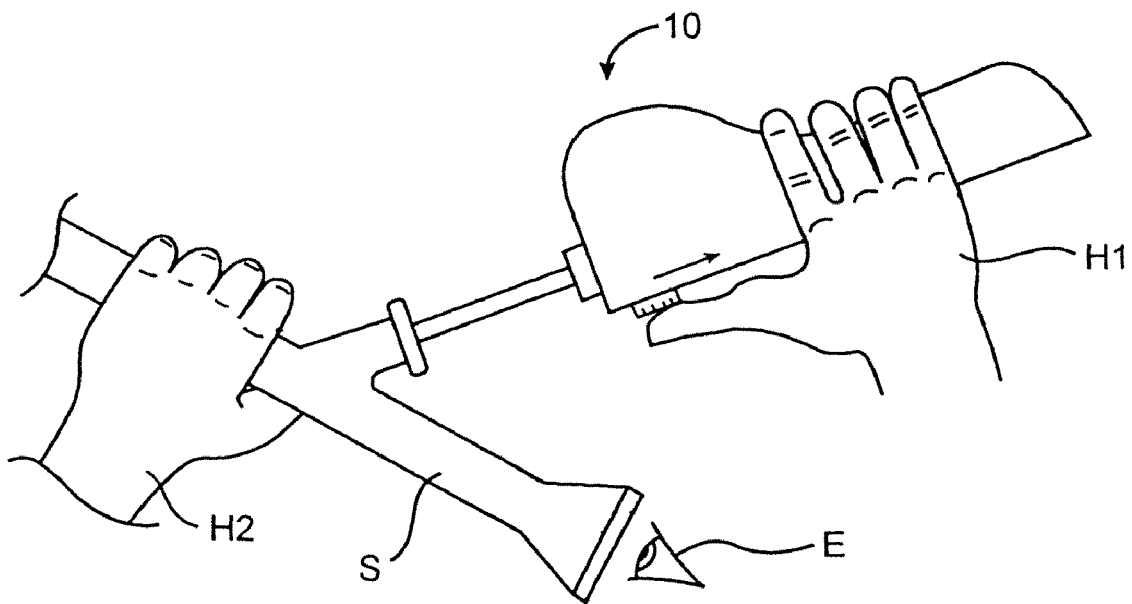
Figure 11B:
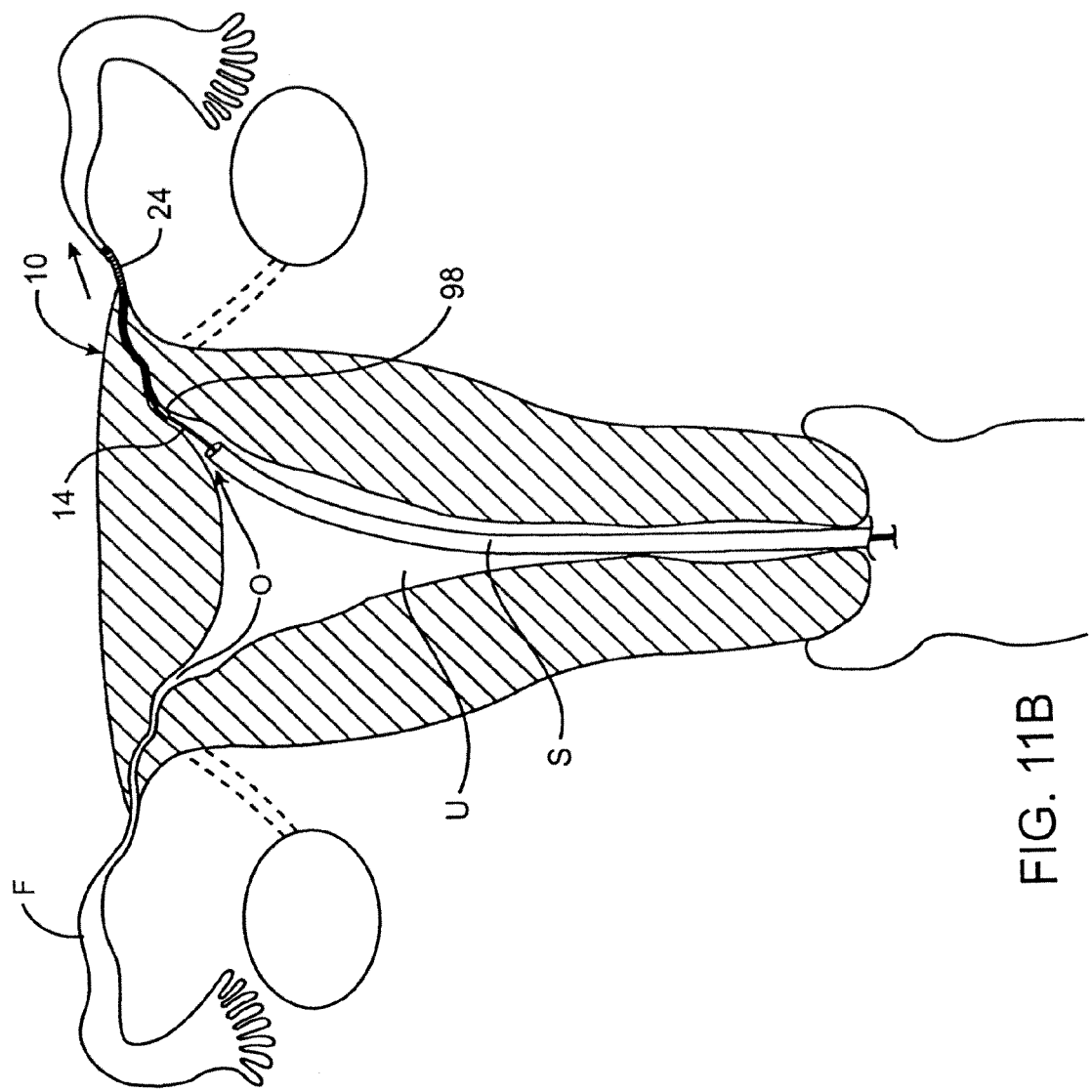

Referring now to FIG. 11B, system 10 is introduced transcervically through uterus U, generally under optical direction. Using hysteroscope S the physician directs the distal end of the system toward ostium O of fallopian tube F. Uterus U may be irrigated and/or distended using scope S and/or a separate irrigation or gas insufflation system. Once ostium O is located and the scope S is oriented toward the ostium, system 10 is advanced distally through the working lumen of the scope and into the ostium using distal portion 24 of the contraceptive device as a guidewire, while the remainder of the contraceptive device remains covered by sheath 14.

The outer hydrophilic coating of sheath 14 minimizes friction while advancing system 10, and the sheath also provides structural column strength to the system. The distal ball tip of distal portion 24 aids tracking and navigation through fallopian tube F, while the primary coil structure flexes laterally to track the tortuous bends often found within the fallopian tube. In the exemplary embodiment, core wire 18 extends into distal portion 24 to enhance column strength of the distal portion beyond sheath 14, but does not extend to the ball tip. Hence, the stiffness of distal portion 24 increases proximally, further enhancing the distal portion's ability to track the lumen.

In the exemplary embodiment, sheath 14 includes a visual marker 98 which can be seen from the scope of hysteroscope S. Marker 98 will preferably be positioned partially within ostium O and partially within uterus U, thereby indicating that contraceptive device 12 is disposed at the target position, as the sheath, core shaft, and contraceptive device are releasably locked together during advancement and positioning an opening (as the sheath, core shaft, and contraceptive device are releasably locked together during advancement and positioning). As described above, marker 98 may comprise a bumper, a structure which extends radially from the sheath to provide a tactile positioning indication.

Figure 11C:
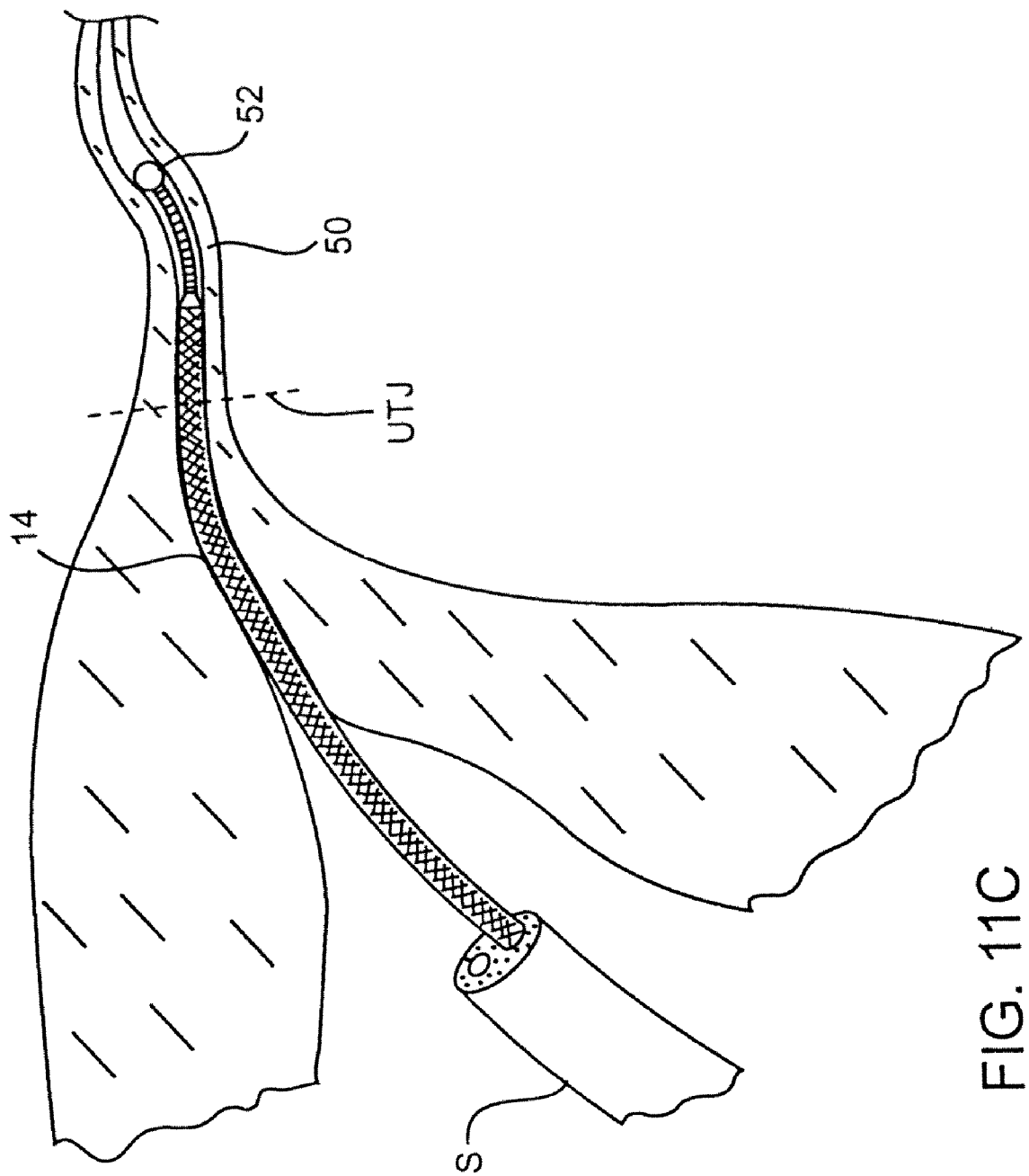

Preferred positioning of contraceptive device 12 is illustrated in FIG. 11C. Preferably, device 12 extends across the uterotubal junction UTJ, with the device ideally extending both proximally and distally of the uterotubal junction. The intermural section INT (see FIG. 1) typically has a length in a range from about 1 to about 2 cm, and outer coil 56 will preferably extend proximally beyond ostium O into uterus U by a distance in a range from about 0.2 to about 1.2 cm. Outer coil 56 will preferably extend distally of the intermural section INT and/or uterotubal junction UTJ by a distance of at least about 0.6 cm. As the uterotubal junction UTJ is adjacent muscular tissues which are soften higher in strength than the delicate tubal tissues of the more distal sections of fallopian tube F, the narrowest portion of the fallopian tube (particularly after deployment of device 12) will often be found adjacent the uterotubal junction. Extending the expandable structure both distally and proximally of this narrowing can provide anchoring against proximal and distal movement of the device, thereby avoiding movement of contraceptive device 12 from the target position while tissue ingrowth takes place. Advantageously, positioning accuracy with a range of about 1 cm may be provided by limiting marker 98 to a 1 cm length. This provides a sufficient positional tolerance for ease of use while helping to ensure reliable, well-anchored deployments.

Figure 11D:
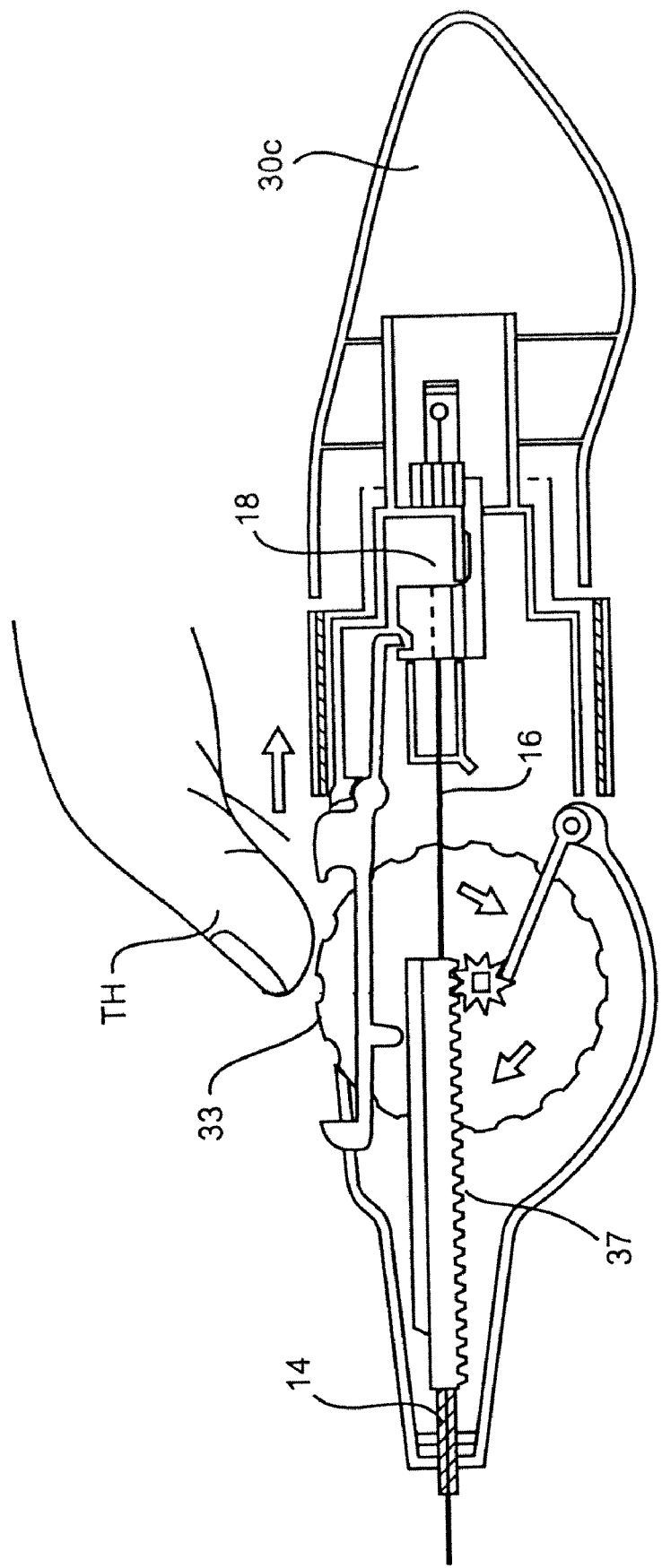
Figure 11E:
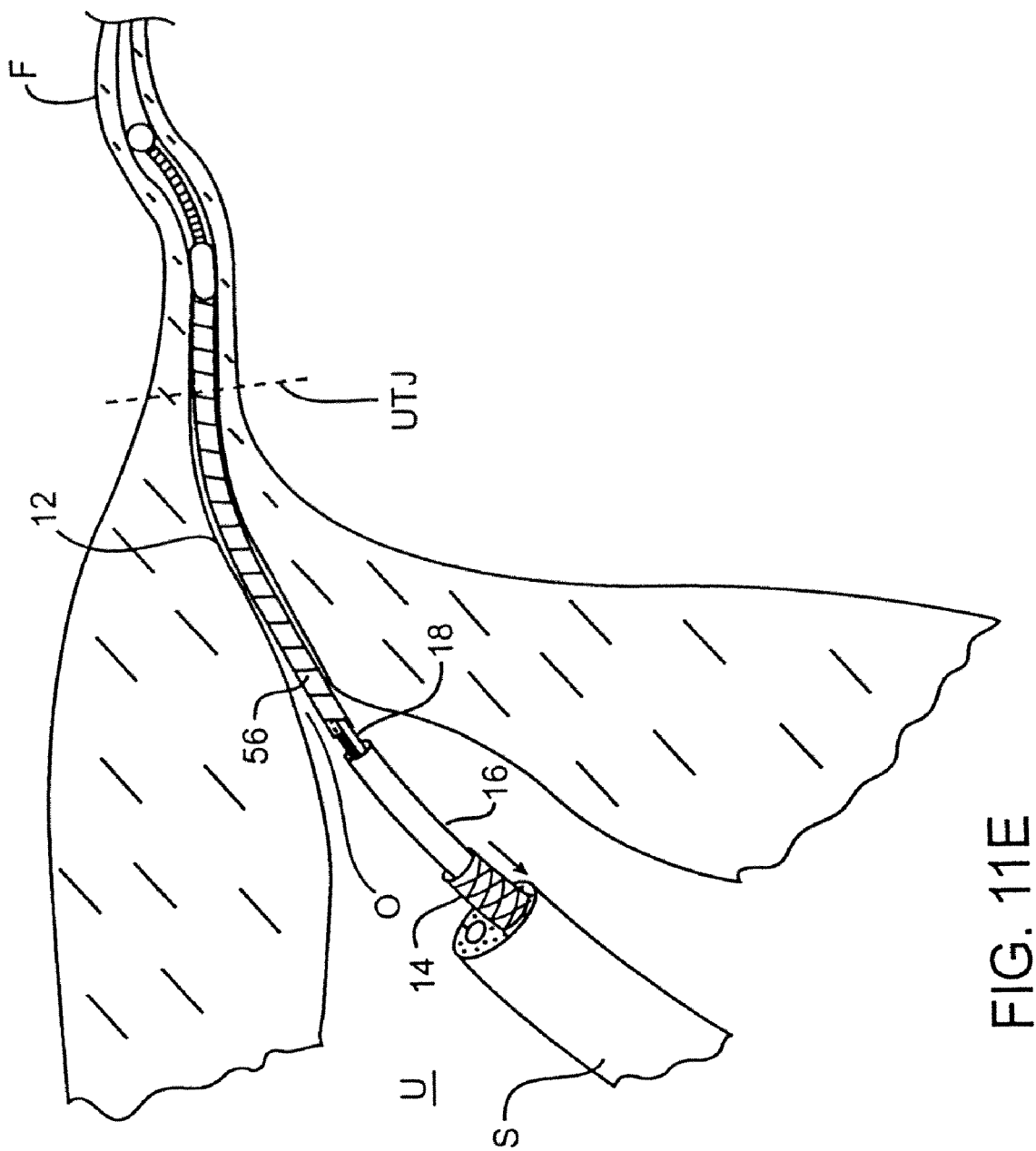

Referring now to FIGS. 11C, 11D, and 1B, positioned contraceptive device 12 is deployed by first withdrawing sheath 14 from over the expandable structure. Using the embodiment of FIG. 10, thumb wheel 33 is rotated proximally by thumb TH to draw sheath 14 proximally from over the contraceptive device. Handle 30 is held in a fixed position, while the thumb wheel is rotated, so that core shaft 18 maintains contraceptive device 12 at the target location within the tubal ostium. Once rack 37 engages the corresponding proximal structure of release catheter 16, further movement of sheath 14 and thumb wheel 33 will be impeded until latch 39 is depressed, as can be understood with reference to FIG. 11B. At this time, device 12 has been positioned at the target location, and sheath 14 has been withdrawn proximally allowing the proximal portion of the contraceptive device to be viewed from Scope so as to verify initial positioning.

Figure 11F:
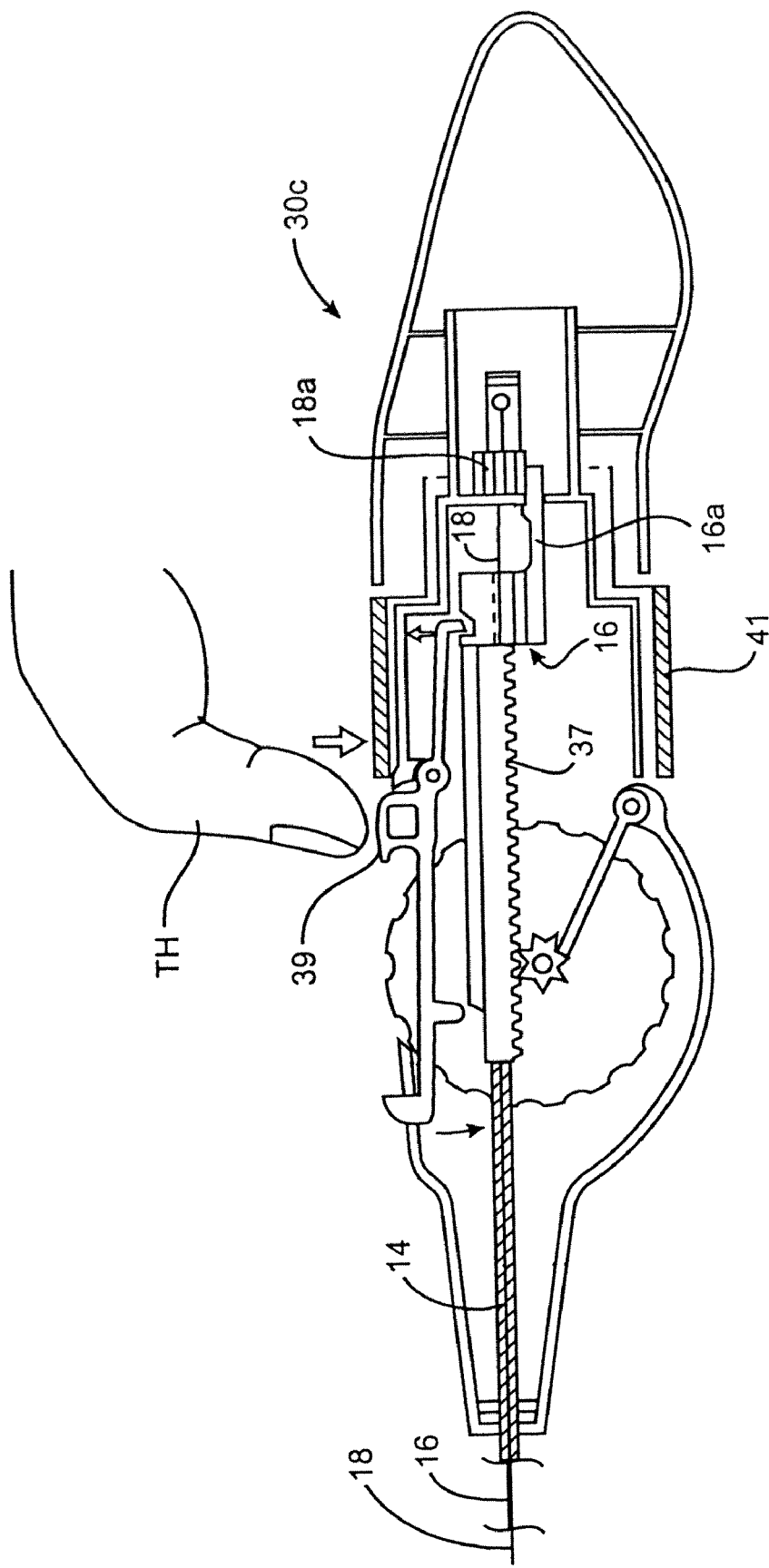
Figure 11G:
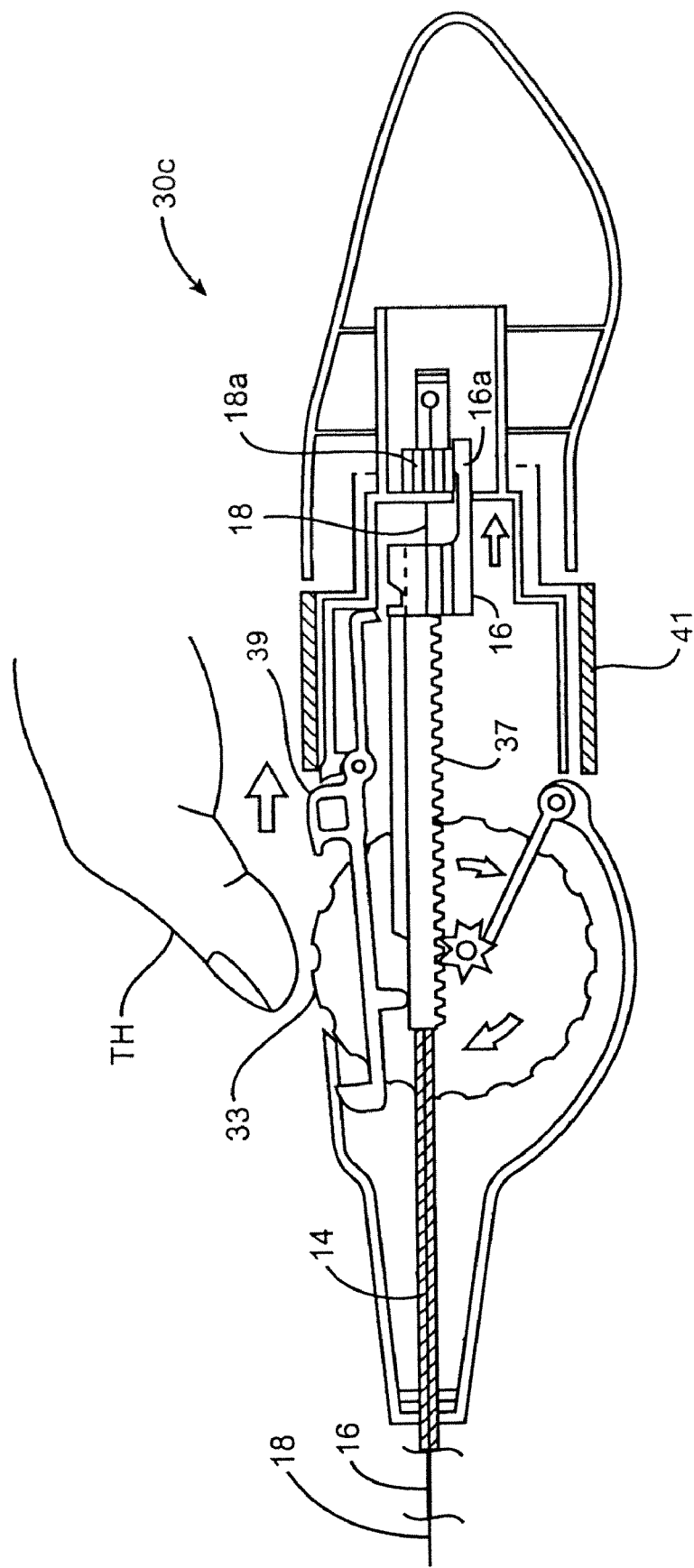
Figure 11H:
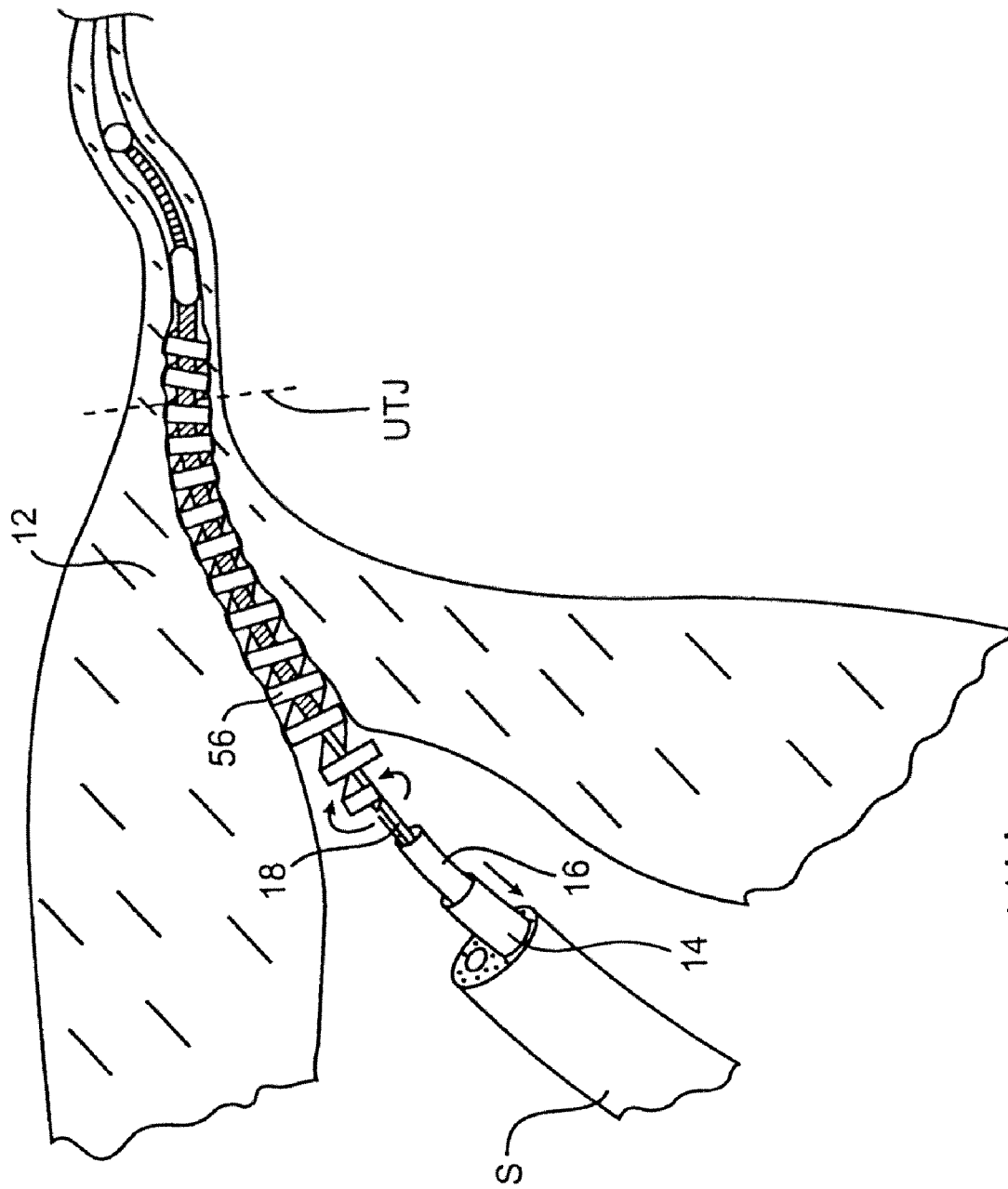

Referring now to FIGS. 11F, 11G, and 11H latch 39 is depressed so as to allow the proximal structure of release catheter 16 to be moved axially by rack 37. After latch 39 is depressed, thumb wheel 33 can again be rotated so as to draw both sheath 14 and release catheter 16 proximally relative to core shaft 18. As seen in FIG. 11H and described above with reference to FIG. 6, this rotationally decouples the outer coil of the contraceptive device from the release catheter 16, allowing the release catheter to expand.

While the dual action thumb wheel and safety latch mechanism illustrated in FIGS. 11F and 11G is preferred, a variety of alternative uncovering/expansion mechanisms may be employed. For example, referring again to FIG. 1B, spring 51 hinders rotation of thumb wheel 33 until latch 39 is depressed. Optionally, spring 51 may store sufficient energy to move release catheter 16 relative to core shaft 18 when latch 39 is actuated, or spring 51 may be entirely absent so that latch 39 allows the thumb wheel to expand the expansible structure by moving both sheath 14 and release catheter 16 relative to the core shaft 18.

Once core shaft 14 has been withdrawn from over the expandable structure and release catheter 16 has been disengaged from the exposed expandable structure resiliently expands and affixes contraceptive device in place, handle 30 may be rotated to disengage the contraceptive device 12 from the remaining components of delivery system 10. Referring once again to FIGS. 11F and 11G, sliding proximal structure 16a attached to proximal end of release catheter 16 proximally allows a proximal structure 18a of core shaft 18 to rotate. More specifically, splines on the proximal structure of the release catheter are moved axially beyond cooperating splines on the proximal structure of the core shaft. The core shaft proximal structure 18a is rotationally coupled to knob 41, so that the cooperating splines prevent rotation of the knob prior to the deployment's stroke of the release catheter, but thereafter allow the knob to be rotated so as to facilitate decoupling of core shaft 18 from the contraceptive device.

Figure 11I:
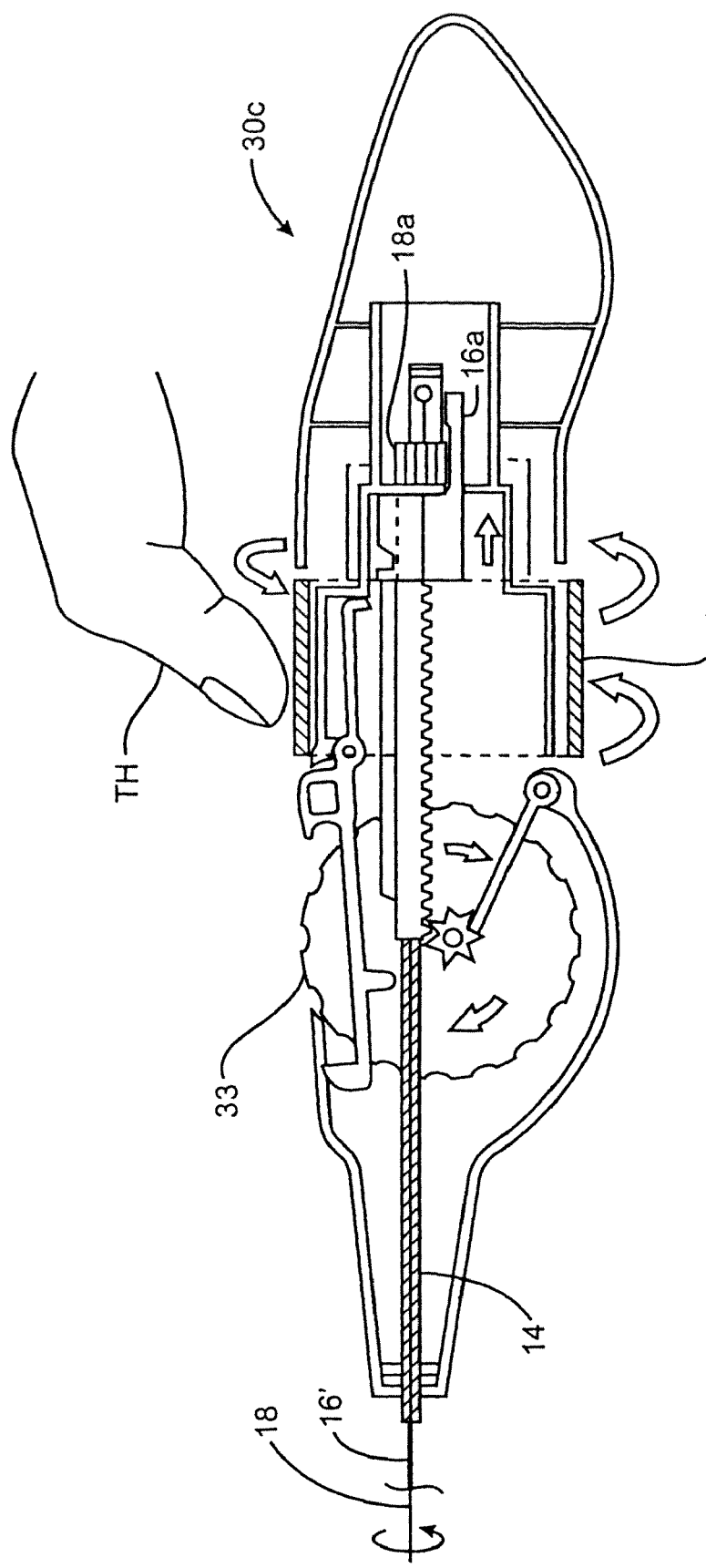
Figure 11K:
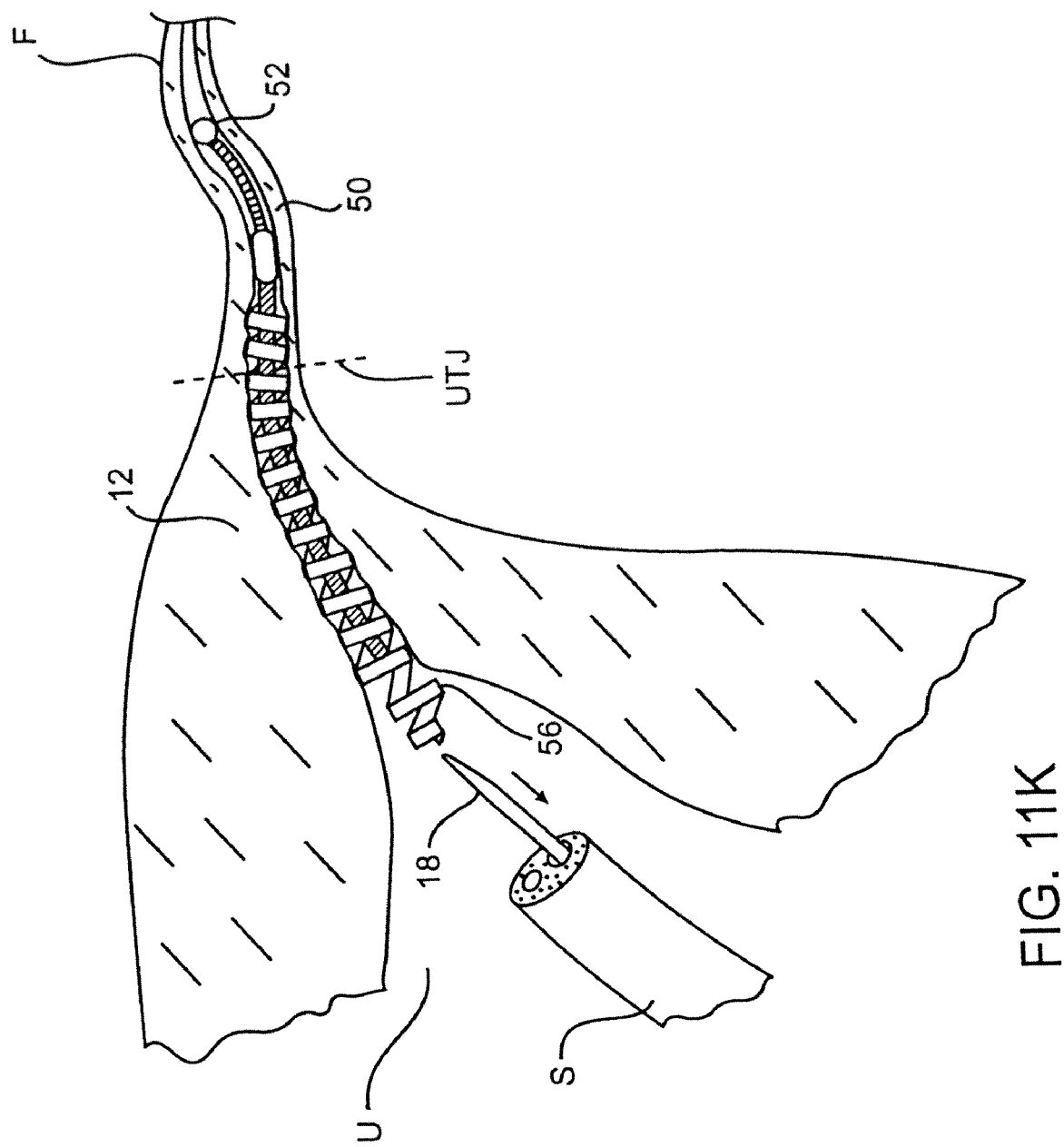

Referring now to FIGS. 11I, 11J, and 11K, once the proximal structures of the release catheter and core shaft 16a and 18a have moved so that knob 41 is free to rotate, the operator rotates the knob using thumb TH and/or the fingers of the hand holding release handle 30C. As described above, the direction of rotation of the core shaft for disengagement will be generally opposed to that imposed by the wind-down torque, so that the wind-down torque helps maintain threaded engagement. Once core shaft 18 is unthreaded from contraceptive device 12, handle 30, sheath 14, release catheter 16, and core shaft 18 may be withdrawn proximally into and/or through the scope S. Scope S may be remain within uterus U and another delivery system may be inserted into the scope for deployment of a contraceptive device in the ostium of the opposed fallopian tube. After deployment of both contraceptive device in the two fallopian tubes, and after the scope is used to visually verify both deployments have been successful, the scope is withdrawn transcervically from the uterus, as illustrated in FIG. 11K.

Figure 12A:
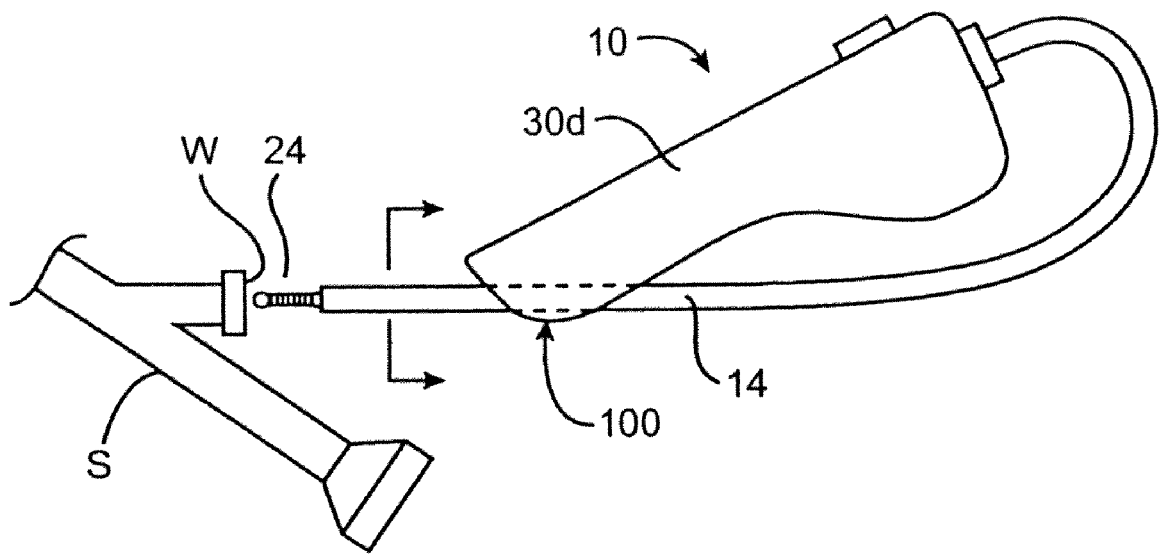
FIGS. 12A and 12B are side and axial end views schematically illustrating the use of an indentation in the handle to facilitate introducing the guidewire-like distal end of the contraceptive delivery system into a lumen, such as the working lumen of a hysteroscope.
Figure 12B:
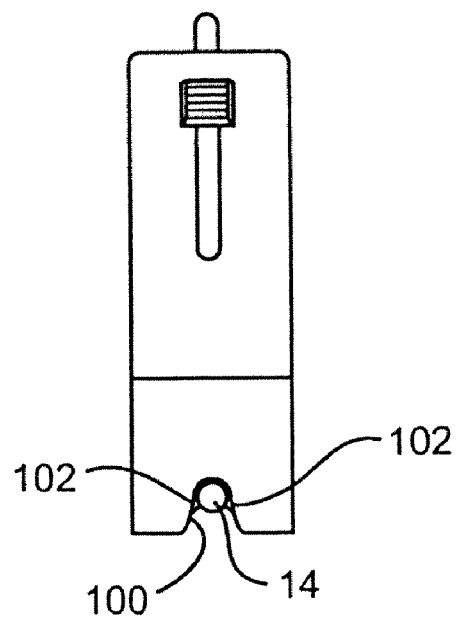

Referring now to FIGS. 12A and B, a slotted handle 30d preferably includes a slot 100 which laterally receives sheath 14 when the distal portion of delivery system 10 is bent as shown. As can be seen most clearly in the view along the distal axis of the delivery system shown in FIG. 12B, slot 100 fittingly receives sheath 14 adjacent the distal end of the delivery system. Detents 102 extend from the housing into slot 100 and restrain sheath 14 within slot 100 against the resilient straightening forces from the sheath, from release catheter 16, and from core shaft 18.

The elongate components of delivery system 10 which extend distally from handle 30d to the distal end of distal portion 24 present an elongate guiding structure with a lateral flexibility which increases distally toward the distal end. By releasably securing this self-guiding structure within slot 100, the guiding structure can be easily inserted into a working lumen W of hysteroscope S using handle 30d. This avoids having a long flexible guidewire-like structure extending in cantilever a considerable distance from the handle, or having the dead weight of the handle flopping uncontrollably while the delivery system is grasped adjacent the distal end of sheath 14 to insert distal portion 24 into the working lumen. Such a structure will have a wide variety of applications for guidewires and guidewire-like structures having proximal handles for facilitating insertion of their distal ends into lumens of vascular access catheters, insertion sheaths, monorail catheter lumens, and the like.

Figure 13:
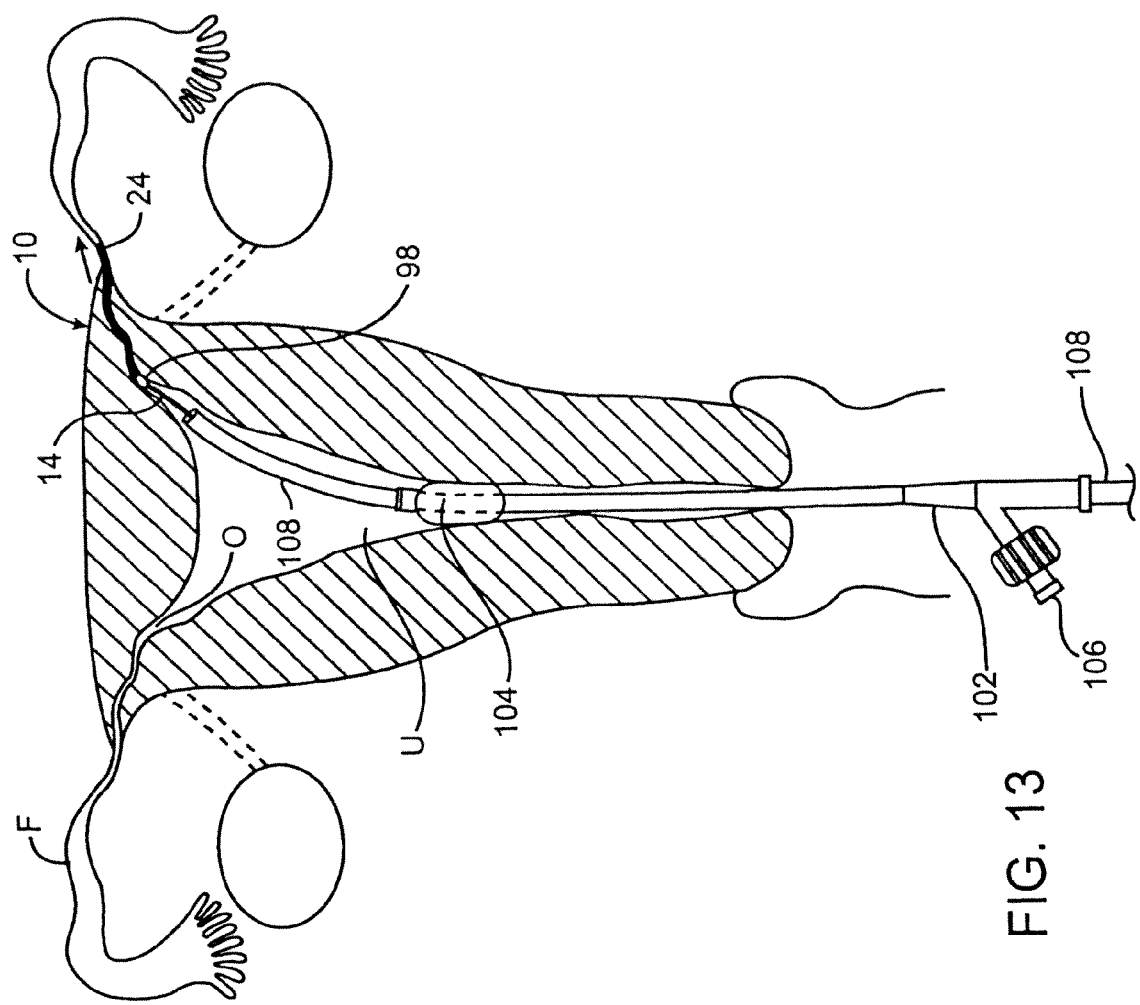
FIG. 13 illustrates an alternative deployment method using an alternative imaging system.

Referring now to FIG. 13, a variety of alternative deployment methods might be used to deploy the contraceptive system 10. For example, using a simple cervical catheter 102, deployment might be directed sonographically, fluoroscopically, under magnetic resonance imaging, and possibly even solely from tactile information. In the alternative exemplary method illustrated in FIG. 13, a balloon 104 of cervical catheter 102 is inflated via inflation port 106. This allows the uterus U to be distended by introduction of distention media through a uterine catheter 108 inserted through the working lumen of cervical catheter 102. Preferably, anatomy and target location identification, device positioning, deployment, detachment, and position confirmation (as outlined in method 2 with reference to FIG. 1A) is performed under the guidance of ultrasound and/or fluoroscopic imaging. Relevant uterine catheter manipulation structures and methods are described in U.S. Pat. Nos. 5,346,498; and 5,389,100, the full disclosure of which are incorporated herein by reference.

As described above, the delivery systems of the present invention will often hold the contraceptive device in a fixed position while the contraceptive device is uncovered, expanded, and/or released. When moving, for example, outer sheath 14 so as to expose the proximal portion of the contraceptive device, friction between the outer sheath and the surrounding hysteroscope (or other introducing structure, surrounding tissue, or the like) may cause inadvertent movement of the contraceptive device. To avoid such inadvertent movement, an outer sleeve may be slidably disposed around outer sheath 14. The sleeve provides a sliding interface between the sheath and surrounding structures. By axially coupling the sleeve and core shaft 18, friction between the sleeve and surrounding structures may inhibit movement of the contraceptive device.

Figure 14A:
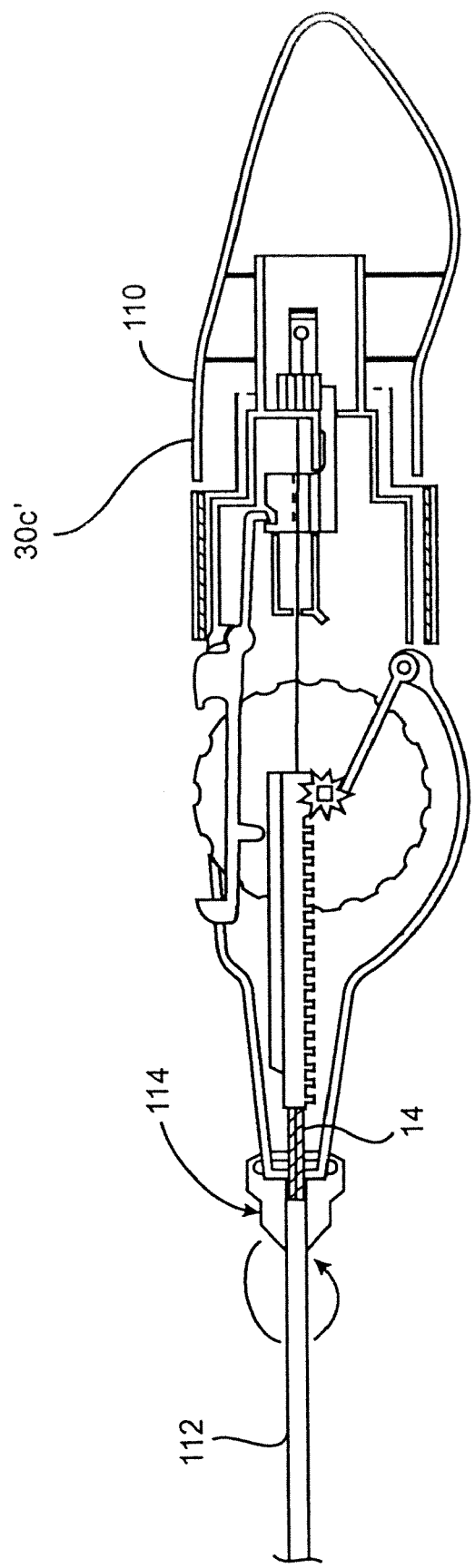
FIGS. 14A and 14B illustrate a deployment system having a sleeve disposed around the outer sheath, and use of the sleeve to inhibit inadvertent movement of the contraceptive device when the outer sheath is retracted.
Figure 14B:
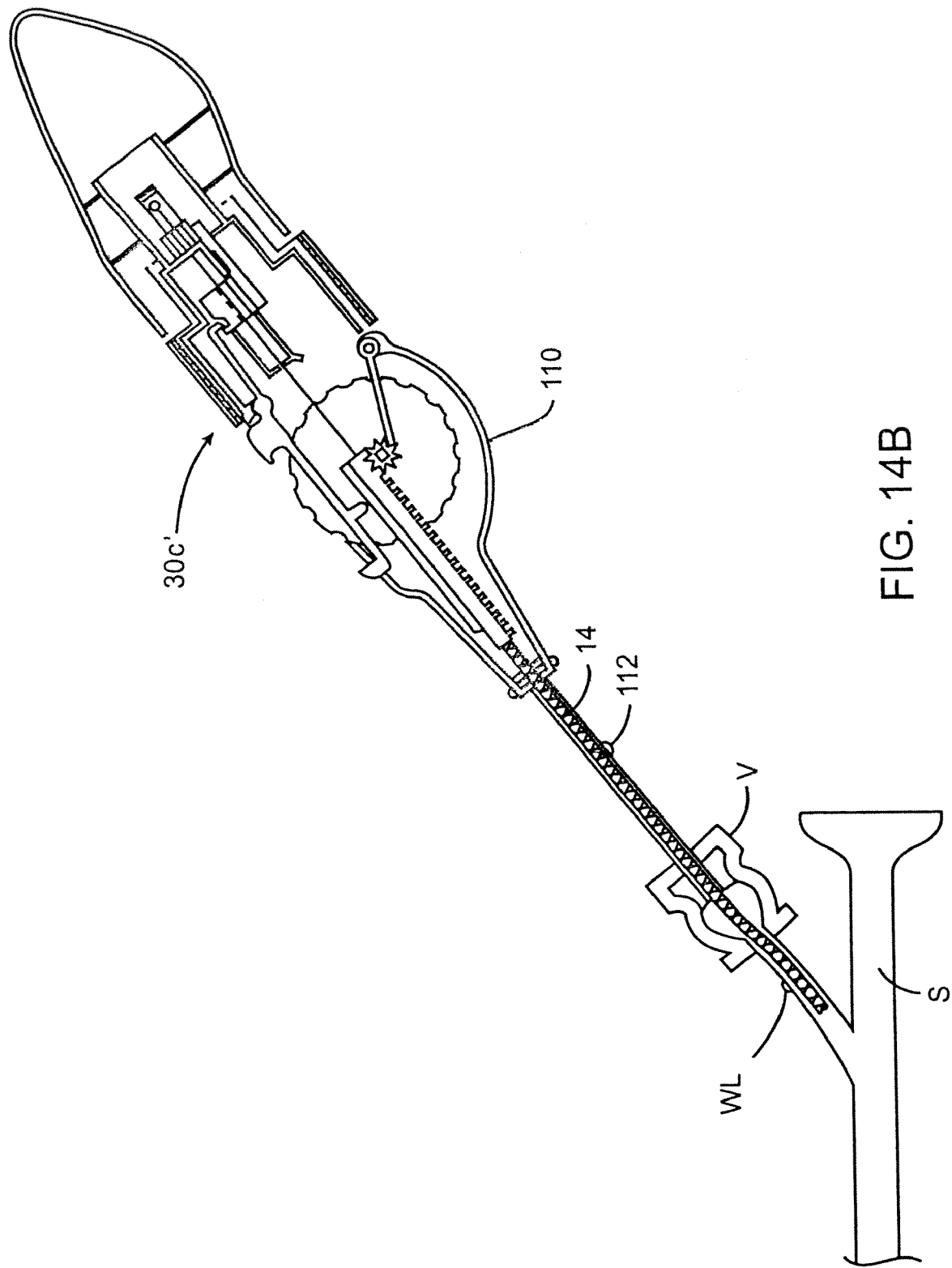

Referring now to FIGS. 14A and 14B, a sleeve 112 is slidably disposed around at lease a proximal portion of sheath 14. Sleeve 112 is axially restrained relative to core shaft 18 by axially connecting the proximal end of the sleeve to housing 110 of handle 30c', optionally using a rotatable connector 114 (to allow the sleeve to rotate relative to the housing). Sleeve 112 will often have a distal end disposed proximally of contraceptive device 12.

As can be seen in FIG. 14B, sleeve 112 will often advance into a sealing introducer structure such as a nipple value V of hysteroscope S. Sleeve 112 may also extend at least through the bend where a working lumen WL of the hysteroscope joins the main shaft of the scope. Sleeve 112 allows independent movement of sheath 14 despite frictional engagement between the sleeve and nipple valve V, and between the sleeve and working lumen WL. Rotatable connector 114 allows free rotation of handle 30c' (and core shaft 18) during disengagement of the core shaft from the contraceptive device.

Figure 15:
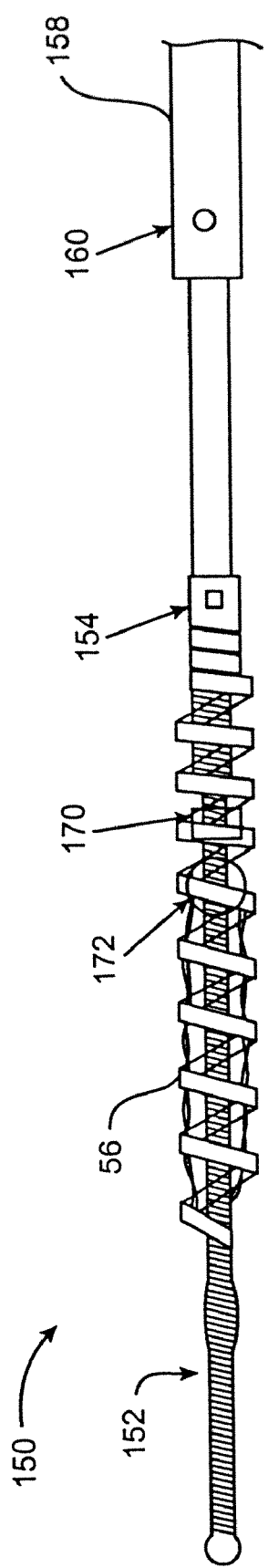
FIG. 15 schematically illustrates a side view of alternative distal components for a contraceptive system.
Figure 16:
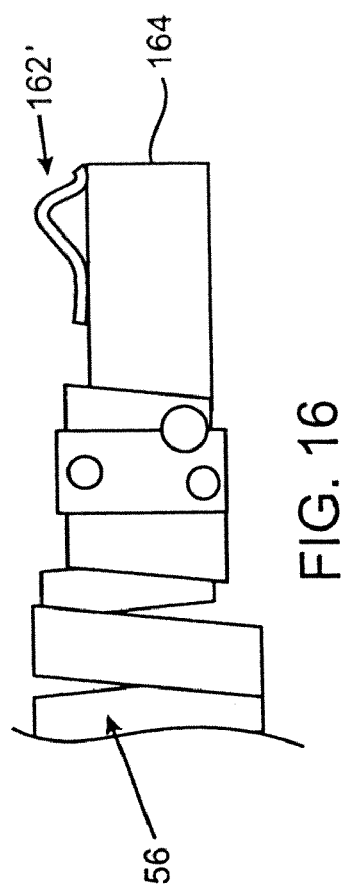
FIG. 16 illustrates an alternative coupling structure at a proximal end of an outer helical coil used in the alternative contraceptive system of FIG. 10.

Referring now to FIGS. 15 and 16, an alternative contraceptive system 150 includes a contraceptive device 152 having many of the components described above, but having an alternative wind-down outer coil connector 154 disposed at a proximal end of outer coil 56. An alternative release catheter 158 having a corresponding connector 160 for engagement with connector 154 of contraceptive device 152 again allows a wind-down torque to be releasably maintained, as described above. In this embodiment, wind-down connector 160 of release catheter 158 comprises an opening which receives a protrusion 162 extending radially from a tubular band of connector 154. These alternative connectors, as well as further alternative threaded connectors 170, 172 for releasable engagement between the primary coil and core wire, are more fully described in an application entitled "Insertion/Deployment Catheter System for Intrafallopian Contraception" (previously incorporated herein by reference), which is filed concurrently herewith. One or more of these connector structures will preferably provide a high contrast image under at least one known medical imaging modality. Such markers can help positioning of contraceptive device 150, and/or verification of disengagement between corresponding connectors (particularly when each of the engaging connectors in a connector pair provides a high imaging contrast).

Figure 17:
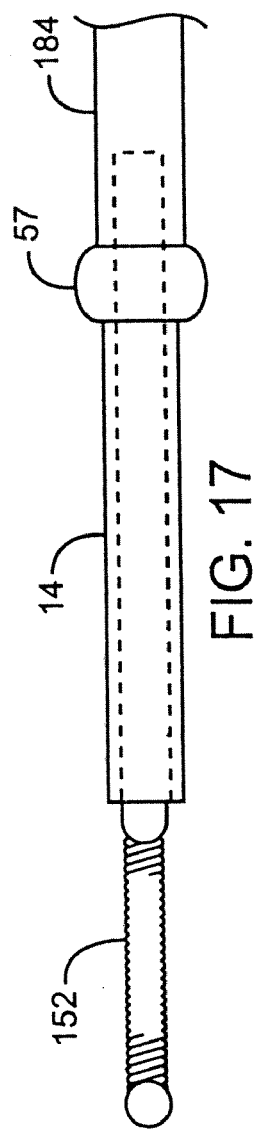
FIG. 17 schematically illustrates a contraceptive system having a separate positioning catheter slidably disposed over the sheath, the positioning catheter having a positioning surface to assist in axially positioning of the contraceptive device.
Figure 18:
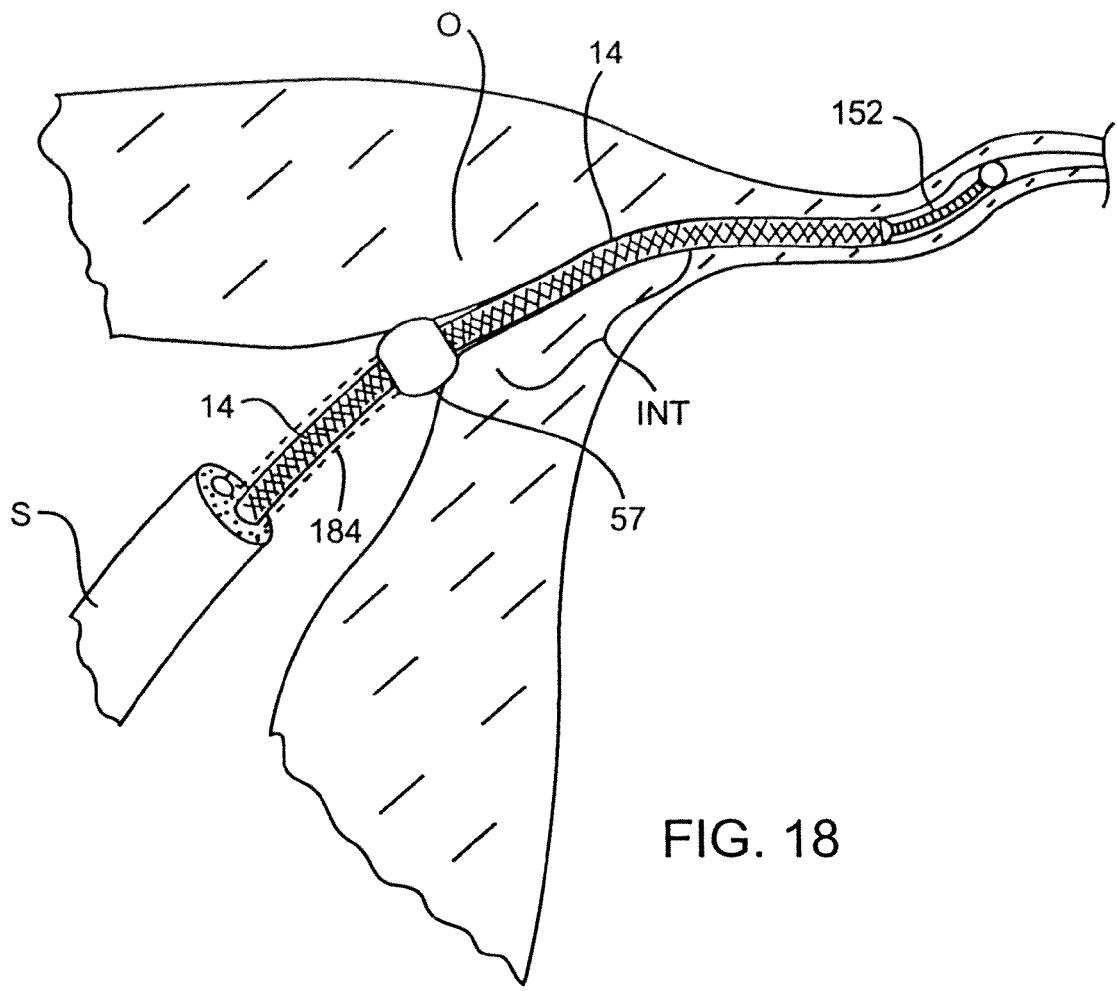
FIG. 18 illustrates a method for using the positioning surface of a sheath or positioning catheter to assist in axially positioning of the contraceptive device.

Referring now to FIGS. 17 and 18, positioning surface 57 may optionally be affixed to sheath 14 to help axially position contraceptive device 152 across intermural region INT, as described above. Engagement between radially protruding positioning surface 57 and the uterine tissue surrounding ostium O facilitates initial axial positioning by taking advantage of the axial coupling of sheath 14 to the contraceptive device. However, sheath 14 will often be withdrawn proximally into scope S early-on during deployment, and it is often desirable to maintain the axial position of the contraceptive device at least until proximal coil 56 begins to expand radially.

As schematically illustrated in FIG. 17, by affixing axial positioning surface 57 (which may optionally comprise any of the alternative positioning surface configurations described hereinabove, or still further alternative structures) at a distal end of a separate positioning catheter 184 slidably disposed over sheath 14, the axial positioning provided by the positioning surface may be maintained during and/or after withdrawal of sheath 14.

Figure 19:
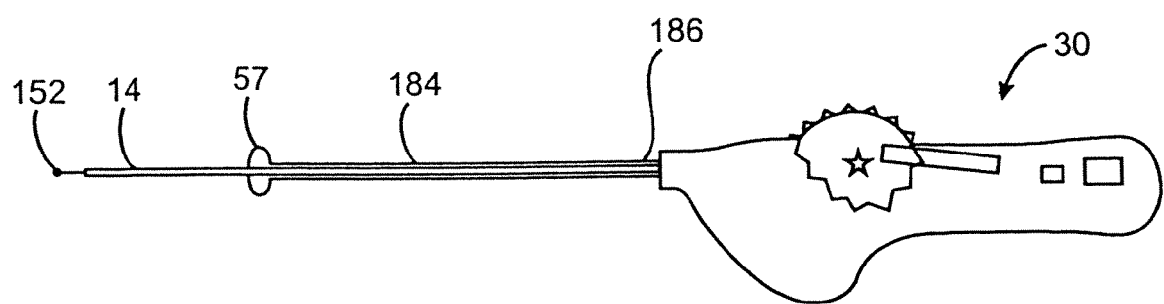
FIG. 19 schematically illustrates a side view of a contraceptive system, showing axially coupling of the positioning catheter to the contraceptive device.

Referring now to FIGS. 17 and 19, a proximal portion 186 of positioning catheter 184 may be axially coupled to a distal portion of handle 30. This arrangement is fairly easy to manufacture, and effectively axially couples contraceptive device 152 to positioning surface 57 via handle 30. Alternatively, positioning catheter 184 may be axially coupled to the release catheter within sheath 14, or to any of the other axially elongate delivery system components extending distally from the handle.

Note that if positioning surface 57 extends distally of the proximal end of outer coil 56, it is possible that the proximal portion of the outer coil will expand partially in the positioning catheter, particularly where the positioning catheter is affixed axially to handle 30 and handle 30 is affixed axially to the core wire. Axial coupling of the positioning catheter to the release catheter (rather than the core wire) may allow at least partial withdrawal of the positioning catheter prior to expansion of the outer coil. In some embodiments, a distal portion of positioning catheter 184, positioning surface 57, and/or a proximal portion of outer coil 56 may be adapted so as to facilitate proximal withdrawal of the positioning catheter after the outer coil has expanded, such as by limiting a diameter of a proximal portion of the outer coil, providing a low friction surface along an inner lumen of the release catheter and/or along the outer surface of the proximal portion of the outer coil, or the like. Fortunately, the relatively high friction outer surface of the distal portion of outer coil 56 within the ostium of the fallopian tube will help inhibit axial movement of the contraceptive device after sheath 14 is withdrawn proximally.

Figure 20:
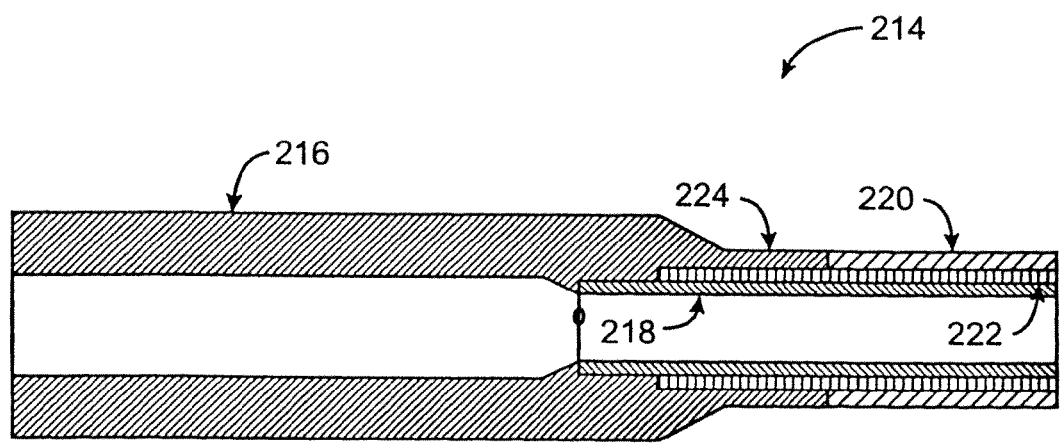
FIG. 20 schematically illustrates a lateral cross-section of an alternative outer sheath of the delivery system of FIG. 1B.

Referring now to FIG. 20, an alternative outer sheath 214 may be used in place of outer sheath 14 in the system of FIG. 1B. Sheath 214 has a proximal portion 216 with a relatively stiff, thicker-walled tubular structure, such as a PeBax® polymer tube having an outer diameter of about 0.062", and an inner diameter of about 0.042". A distal portion of sheath 14 includes an inner tube 218 of a low friction polymer and an outer tube 220 of a polymer, (such as Carbothane™ 73A) with at least one ribbon coil 222 therebetween. Inner tube 218 may comprise a PTFE (such as a Teflon® material) with an inner diameter of about 0.034" and a wall thickness of about 0.001" with the outer diameter etched, and a length of about 5.0 cm, while there are preferably two counterwound ribbon coils 222 of a superelastic or shape memory alloy, such as nickel titanium (optionally with chromium) of about 0.007" by about 0.010" with a pitch of about 0.015" and a length of about 4.0 cm. Inner tube 218 might alternatively comprise ETFE, gamma stable PTFE, FEP, or the like, while ribbon coils 222 may comprise a stainless steel or other medical grade materials. An inner diameter of the distal portion may be about 0.034", with the distal outer diameter of sheath 214 being about 0.041". An intermediate outer tube 224 may comprise a polyurethane having a durometer of about 55. A length of outer tube 220 may be about 1.0 cm, a length of intermediate tube 224 may be about 5 mm, and a length of proximal portion 216 may be about 40 cm.

Figure 21:
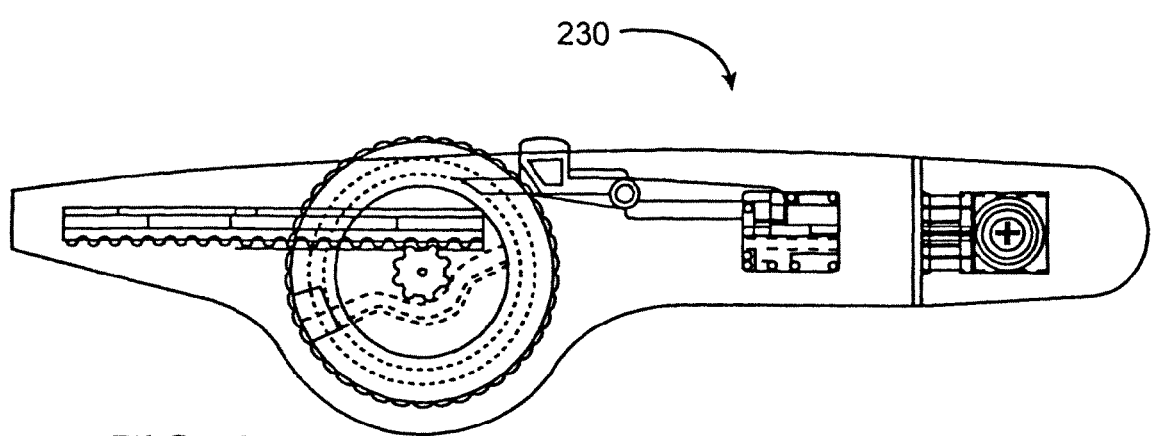
FIG. 21 schematically illustrates an alternative proximal handle of the contraceptive system.

Referring now to FIG. 21, a still further alternative proximal handle 230 includes many of the axial movement components of handle 30c, as described above. Rather than providing a rotatable knob 41, detachment of the contraceptive device from the core wire 18 of the delivery system may be effected by rotation of handle 230 about the axis of the corewire. Still further options are possible, including the detachment of a distal portion of the corewire from the proximal portion, so that the distal portion remains within the contraceptive device after deployment.

While the exemplary embodiment of the present invention has been described in some detail, for clarity of understanding and by way of example, a variety of adaptations, changes, and modifications will be obvious to those who are skilled in the art. Hence, the scope of the present invention is limited solely by the independent claims.

What is claimed is:

1. A contraceptive delivery system comprising:
    a contraceptive device insertable into a female reproductive organ, the contraceptive device having an inner portion and an outer portion surrounding the inner portion, wherein the outer portion is expandable from a small profile configuration to a large profile configuration;
    a release catheter having a proximal end, a distal end and a lumen extending therethrough, wherein the distal end of the release catheter releasably engages the contraceptive device;
    a core shaft extending through the lumen of the release catheter, the core shaft being releasably coupled to the contraceptive device;
    a handle connected with a proximal end of the core shaft, the handle having a size and shape suitable for gripping with a hand;
    a first actuator mounted on the handle, wherein movement of the first actuator by hand causes the contraceptive device to expand and affix to the female reproductive organ; and
    a second actuator mounted on the handle, wherein movement of the second actuator by hand causes the contraceptive device to be decoupled from core shaft.

2. The contraceptive delivery system of claim 1, wherein rotation of the first actuator causes the contraceptive device to expand and affix to the female reproductive organ.

3. The contraceptive delivery system of claim 2, wherein the first actuator comprises a thumb wheel.

4. The contraceptive delivery system of claim 1, wherein rotation of the second actuator releases the contraceptive device from the core shaft.

5. The contraceptive delivery system of claim 4, wherein the second actuator comprises a rotatable knob.

6. The contraceptive delivery system of claim 1, wherein the outer portion is fixed to the inner portion with a bond.

7. The contraceptive delivery system of claim 1, wherein the bond is a solder bond.

8. The contraceptive delivery system of claim 6, wherein the contraceptive device further comprises a flexible distal portion extending distally from the bond to aid in tracking of the contraceptive delivery system in the female reproductive organ.

9. The contraceptive delivery system of claim 8, wherein the contraceptive device further comprises a distal ball tip at a distal end of the flexible distal portion.

10. The contraceptive delivery system of claim 9, wherein the distal ball tip has a diameter in a range from about 0.020 inches to about 0.050 inches.

11. The contraceptive delivery system of claim 8, wherein the bond is separated from the distal ball tip by a distance in the range from about 0.3 cm to about 1.0 cm.

12. The contraceptive delivery system of claim 8, wherein the flexible distal portion comprises stainless steel wire.

13. The contraceptive delivery system of claim 12, wherein the stainless steel wire has a diameter of about 0.005 inches.

14. The contraceptive delivery system of claim 12, wherein the stainless steel wire is wound to form a coil.

15. The contraceptive delivery system of claim 14, wherein the coil has an outer diameter of about 0.022 inches.

16. The contraceptive delivery system of claim 1, wherein the core shaft comprises stainless steel.

* * * * *